(12) United States Patent
Evans et al.

(10) Patent No.: US 6,660,039 B1
(45) Date of Patent: Dec. 9, 2003

(54) MOBILE BEARING KNEE PROSTHESIS

(75) Inventors: David Lee Evans, Bartlett, TN (US); Greg Marik, Germantown, TN (US); Robert Brosahan, Germantown, TN (US); Christopher Patrick, Memphis, TN (US); Albert J. Pothier, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 22 days.

(21) Appl. No.: 10/060,014

(22) Filed: Jan. 29, 2002

Related U.S. Application Data

(63) Continuation-in-part of application No. 09/670,186, filed on Sep. 26, 2000, now Pat. No. 6,428,577, which is a continuation-in-part of application No. 09/082,179, filed on May 20, 1998, now Pat. No. 6,123,728.

(51) Int. Cl.[7] .................................................. A61F 2/30
(52) U.S. Cl. .................................................. 623/20.29
(58) Field of Search ........................... 623/20.14, 20.15, 623/20.21, 20.24, 20.27–20.29, 20.31–20.33

(56) References Cited

U.S. PATENT DOCUMENTS

| | | | |
|---|---|---|---|
| 4,016,606 A | 4/1977 | Murray et al. | |
| 4,094,017 A | 6/1978 | Matthews et al. | |
| 4,216,549 A | 8/1980 | Hillberry et al. | |
| 4,224,697 A | 9/1980 | Murray et al. | |
| 4,340,978 A | 7/1982 | Buechel et al. | |
| 4,673,407 A | 6/1987 | Martin | |
| 5,007,933 A | 4/1991 | Sidebotham et al. | |
| 5,011,496 A | * 4/1991 | Forte et al. | 623/20.27 |
| 5,032,132 A | 7/1991 | Matsen, III et al. | |
| 5,071,438 A | 12/1991 | Jones et al. | |
| 5,116,375 A | 5/1992 | Hofmann | |
| 5,314,483 A | 5/1994 | Wehrli et al. | |
| 5,370,699 A | 12/1994 | Hood et al. | |
| 5,395,401 A | 3/1995 | Bahler | |
| 5,405,398 A | 4/1995 | Buford, III et al. | |
| 5,549,686 A | 8/1996 | Johnson et al. | |

(List continued on next page.)

FOREIGN PATENT DOCUMENTS

| | | |
|---|---|---|
| DE | 4308563 | 9/1994 |
| EP | 0186471 | 7/1986 |
| EP | 4985586 | 8/1992 |
| EP | 636353 | 2/1995 |
| FR | 2672798 | 8/1992 |
| FR | 2698265 | 5/1994 |
| GB | 2219942 | 12/1989 |
| WO | WO 9517860 | 7/1995 |
| WO | WO 9624311 | 8/1996 |

Primary Examiner—Kevin Shaver
Assistant Examiner—Michael B. Priddy
(74) Attorney, Agent, or Firm—Garvey, Smith, Nehrbass & Doody, L.L.C.; Charles C. Garvey, Jr.; Brett A. North

(57) ABSTRACT

A mobile bearing knee prosthesis enables a surgeon to convert a mobile bearing insert having articular surfaces, supported by a tibial base plate or tray from a rotating and translating prosthesis to one that rotates only. This conversion is accomplished with a fastener or locking member that connects through an opening in the insert to the tibial base plate. This prosthesis can be used as part of a total knee surgery when the surgeon chooses to use a prosthesis that incorporates a movable articular surface. In one embodiment, a projecting portion extends proximally from the insert and cooperates with a cam on the femoral component. The projecting portion can be a post extending up from the proximal surface of the insert and the femoral component includes an intercondylar surface that may contact the post to constrain the relative motion between the femoral component and the insert. In another embodiment, the insert is a two part assembly that includes a larger member with a central opening and a smaller member that fits the opening.

24 Claims, 25 Drawing Sheets

U.S. PATENT DOCUMENTS

| | | |
|---|---|---|
| 5,609,639 A | 3/1997 | Walker |
| 5,702,466 A | 12/1997 | Pappas et al. |
| 5,782,925 A | 7/1998 | Collazo et al. |
| 5,871,543 A | 2/1999 | Hofmann |
| 5,871,545 A | 2/1999 | Goodfellow et al. |
| 5,879,394 A | 3/1999 | Ashby et al. |
| 5,906,643 A | 5/1999 | Walker |
| 5,928,286 A | 7/1999 | Ashby et al. |
| 5,935,173 A | 8/1999 | Roger et al. |
| 6,039,764 A | 3/2000 | Pottenger et al. |
| 6,099,570 A | 8/2000 | Livet et al. |
| 6,123,728 A | 9/2000 | Brosnahan et al. |
| 6,165,223 A | 12/2000 | Metzger et al. |
| 6,210,444 B1 | 4/2001 | Webster et al. |
| 6,217,618 B1 | 4/2001 | Hileman |
| 6,238,434 B1 | 5/2001 | Pappas |
| 6,264,697 B1 * | 7/2001 | Walker .................. 623/20.27 |

\* cited by examiner

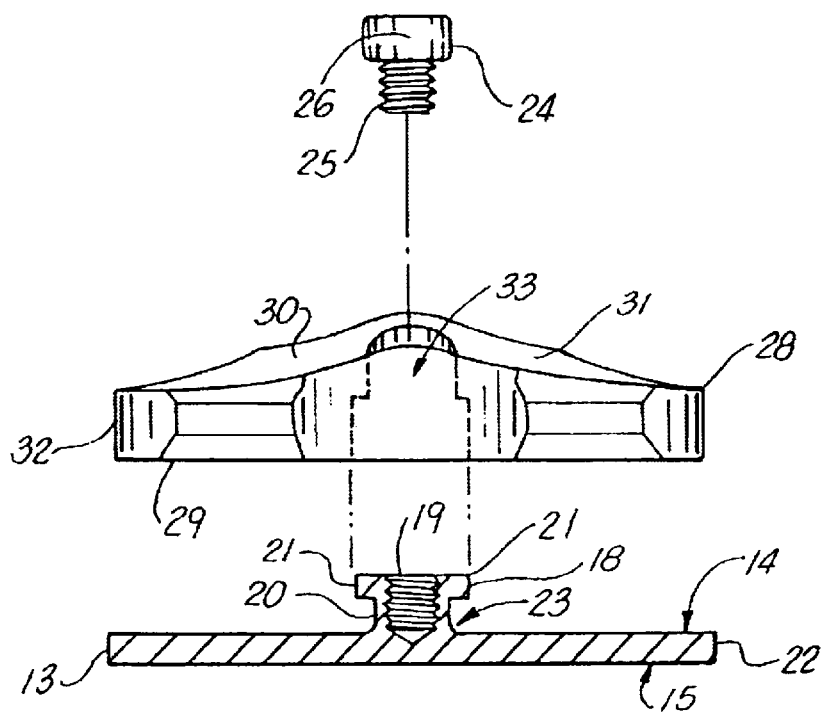
FIG. 5
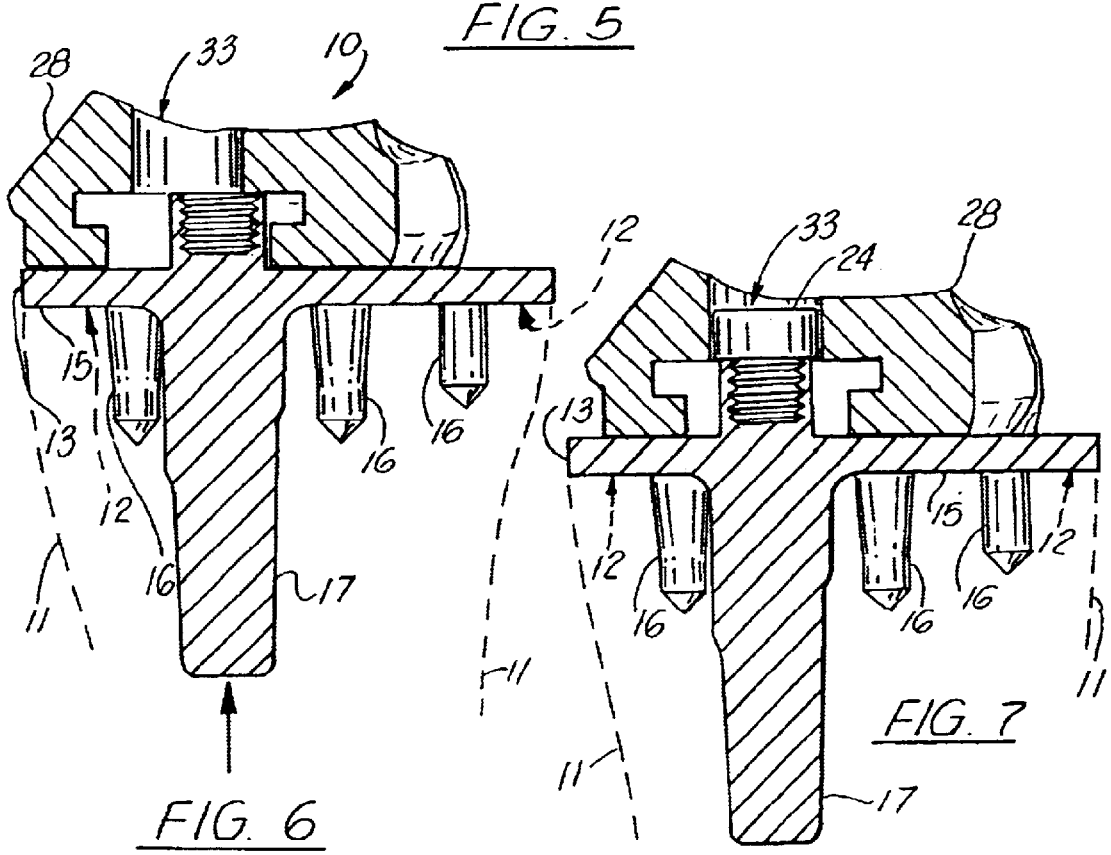
FIG. 6
FIG. 7

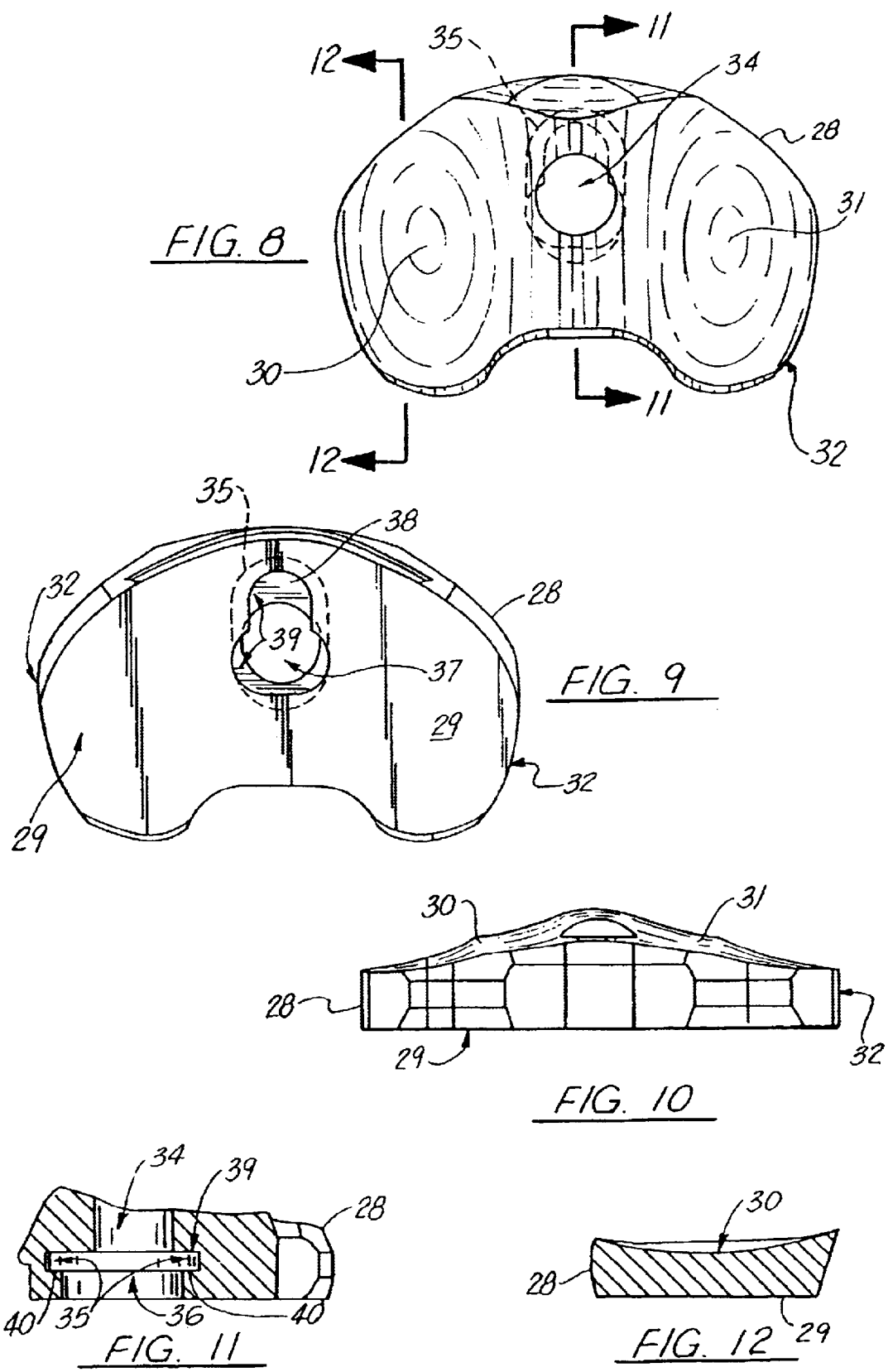

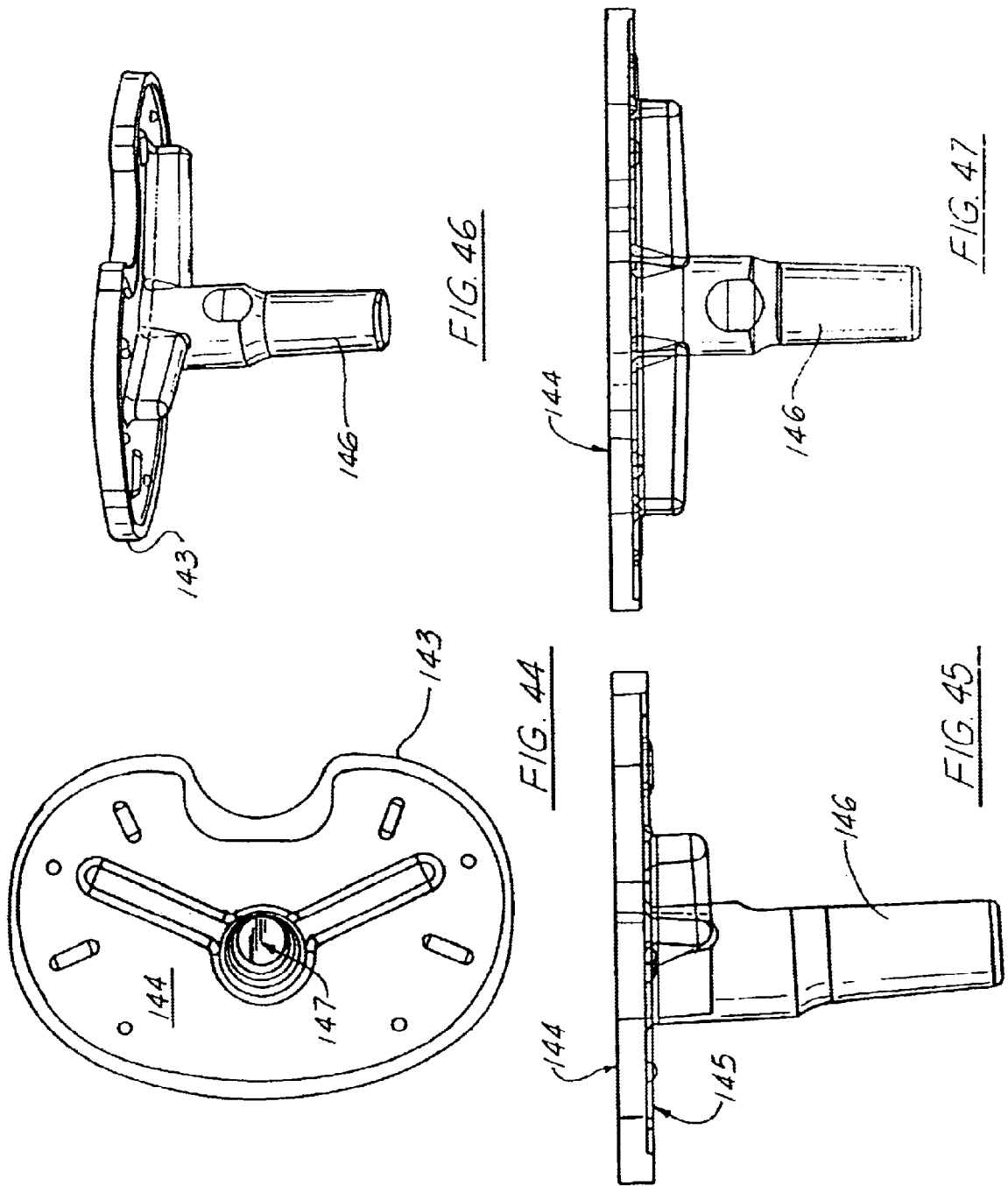

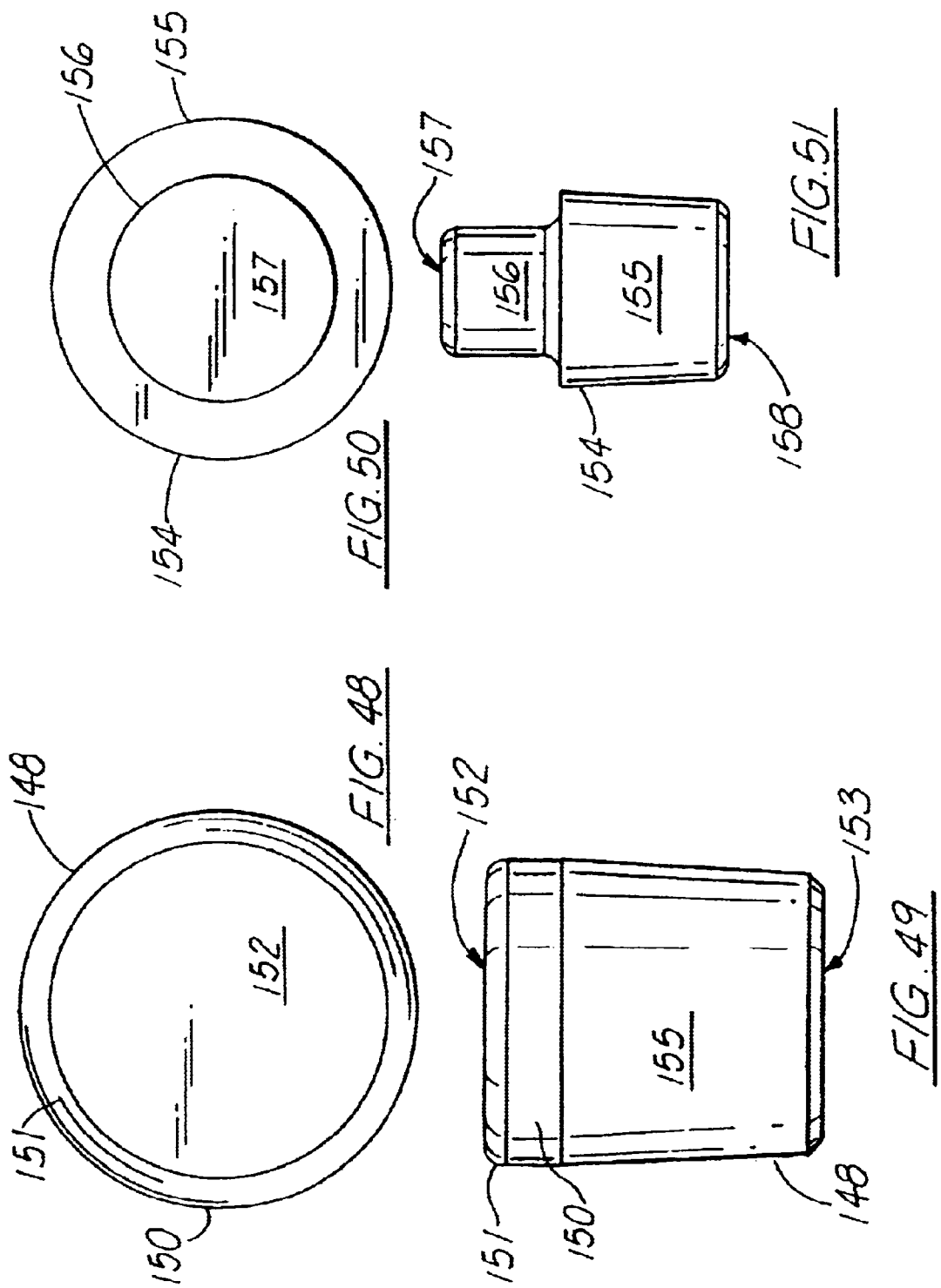

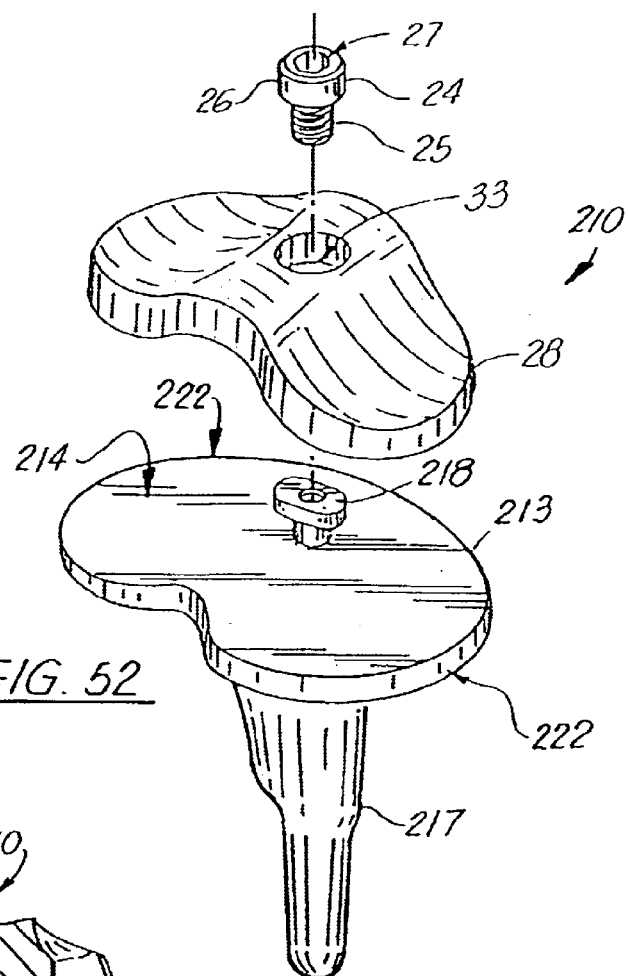
FIG. 52
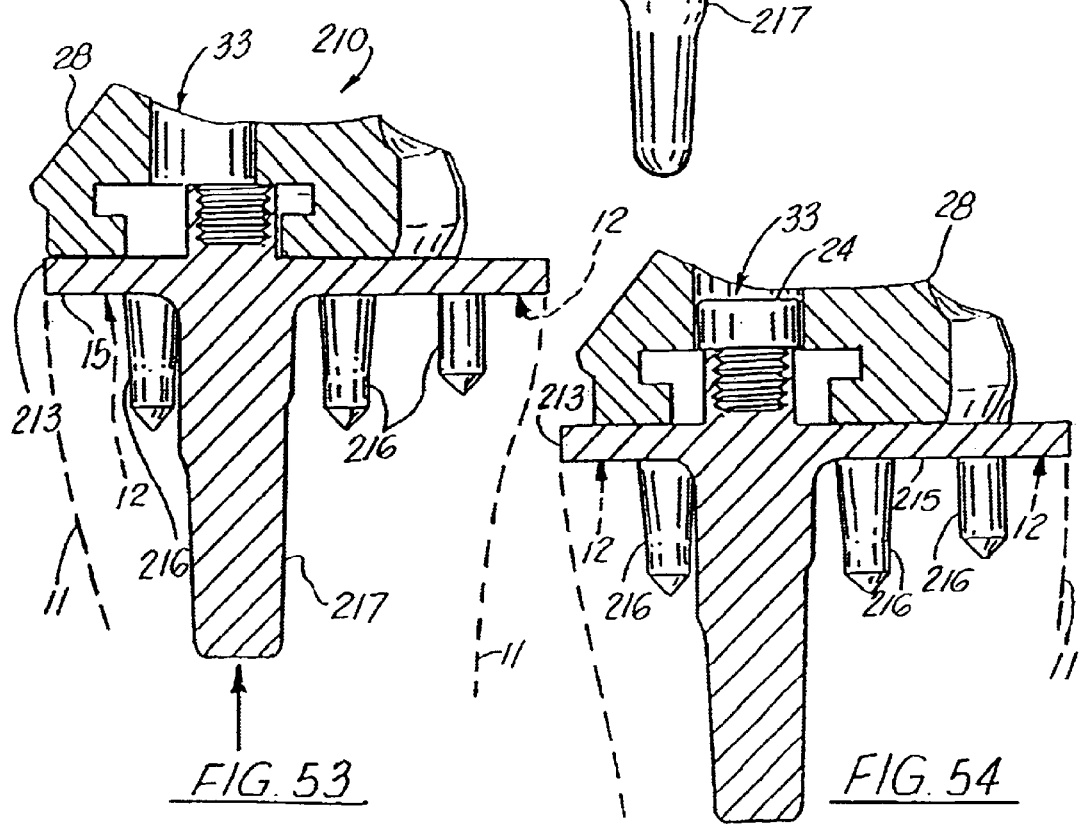
FIG. 53
FIG. 54

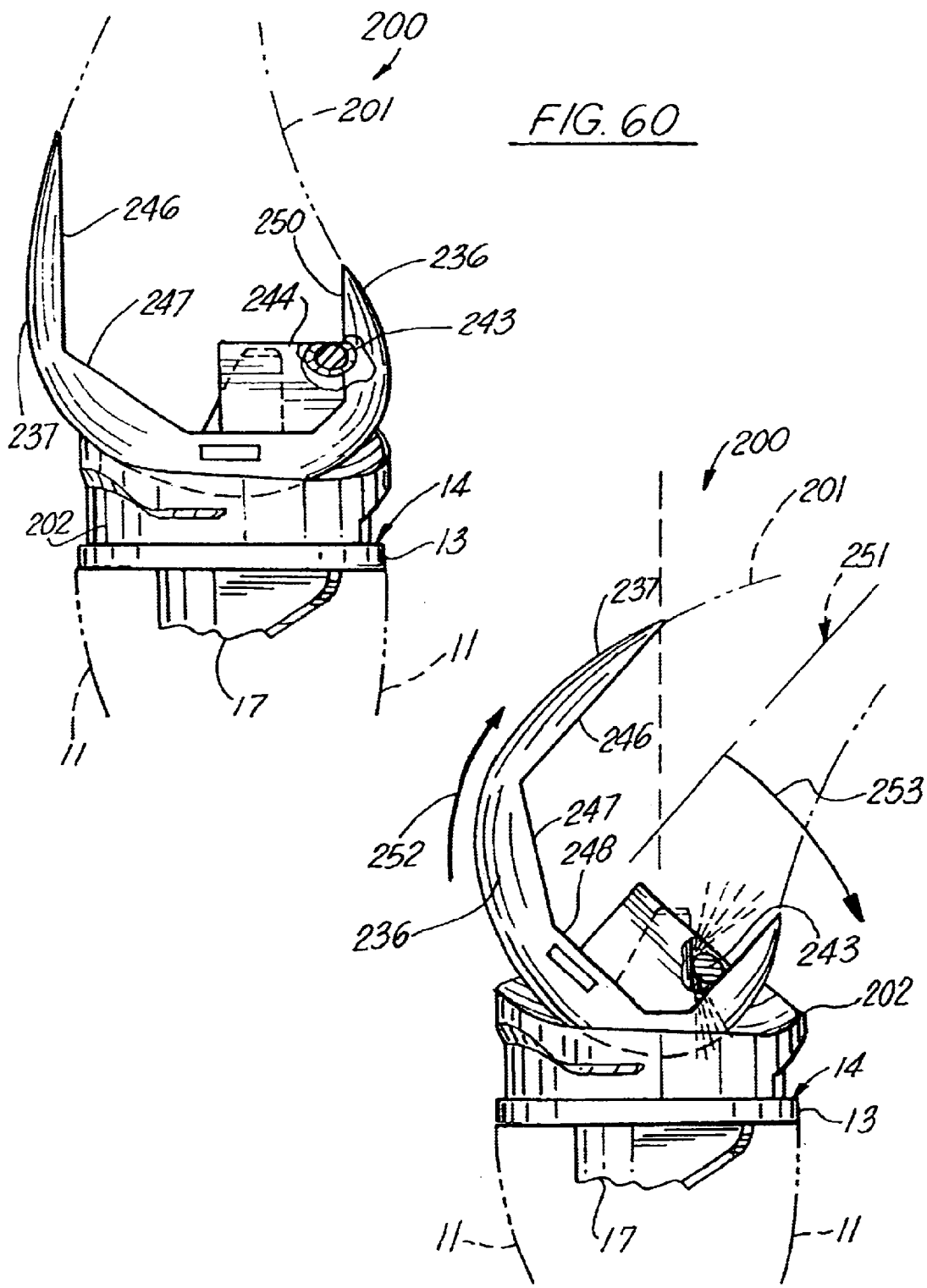

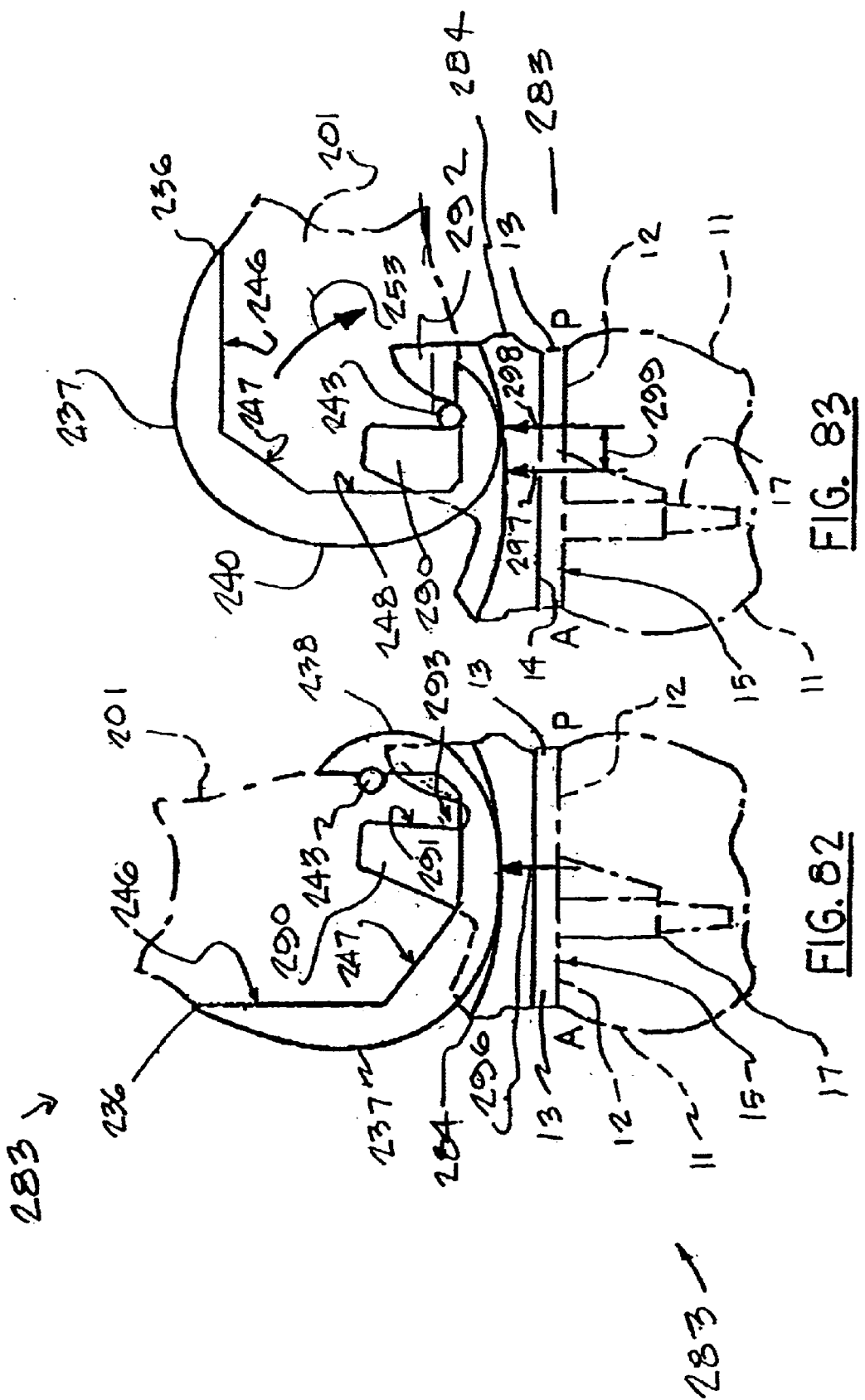

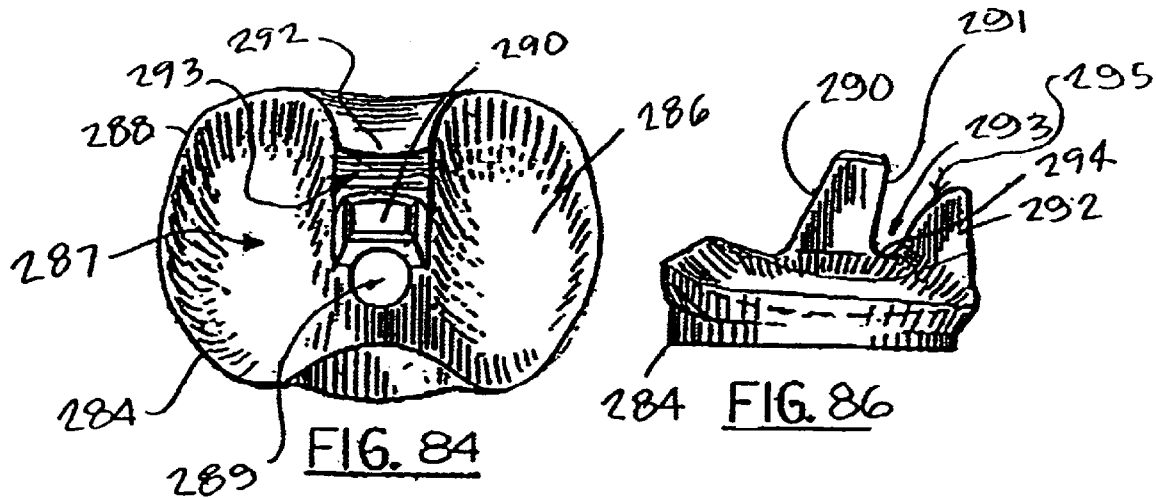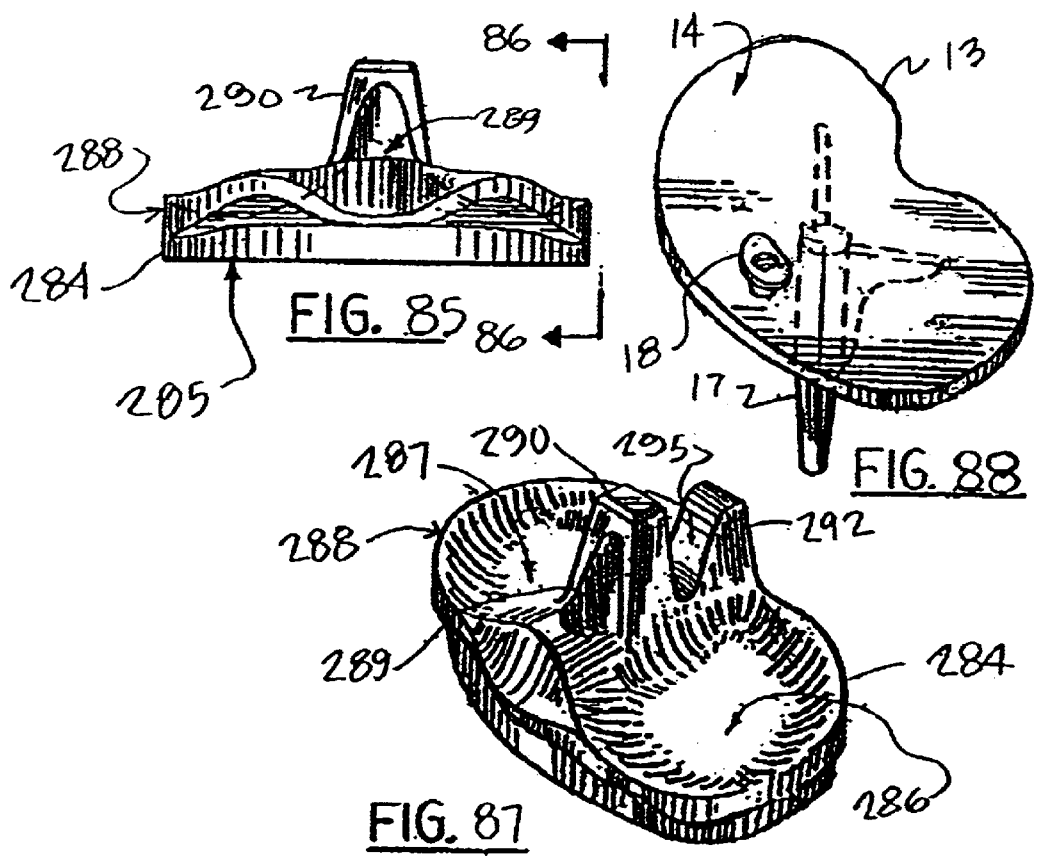

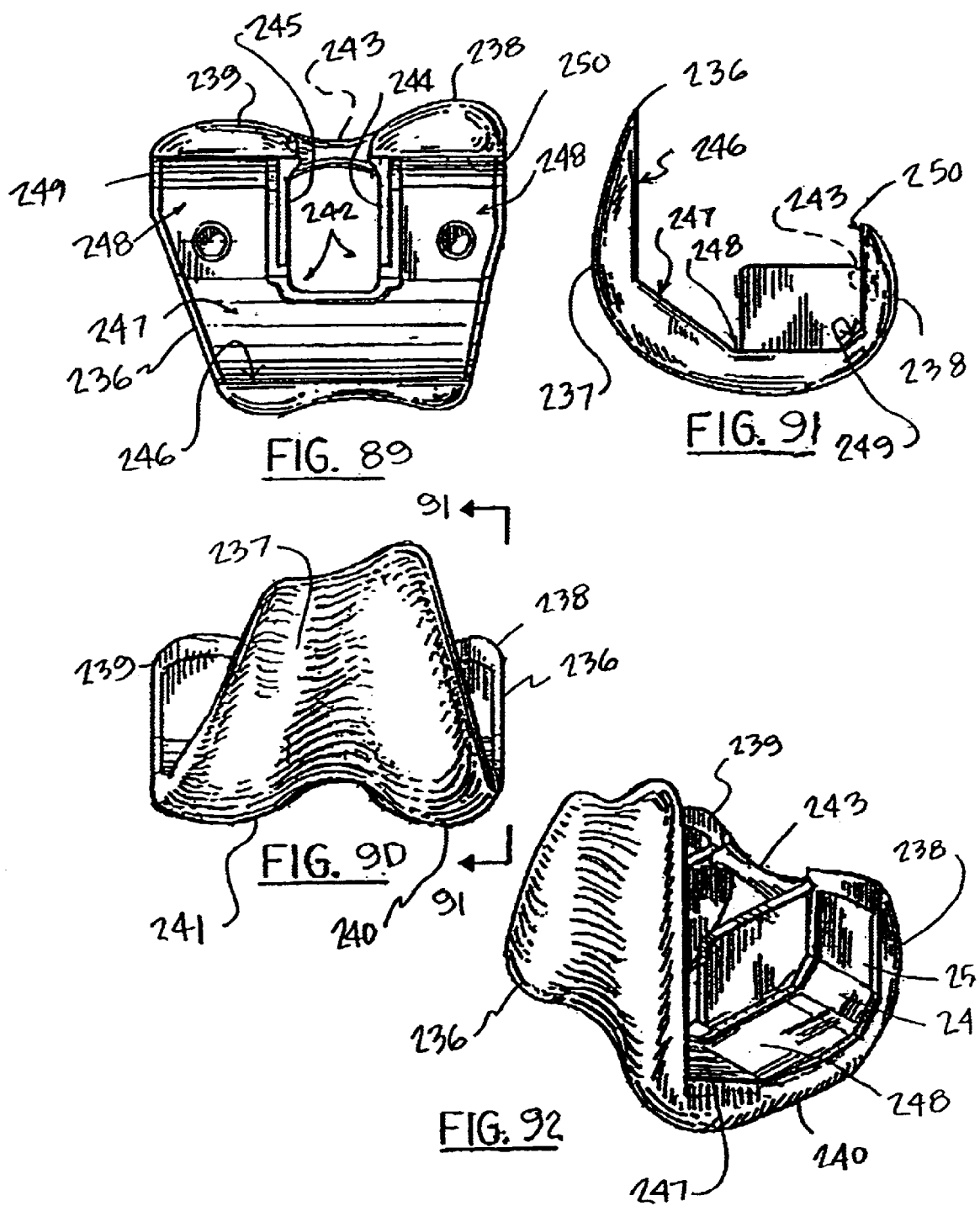

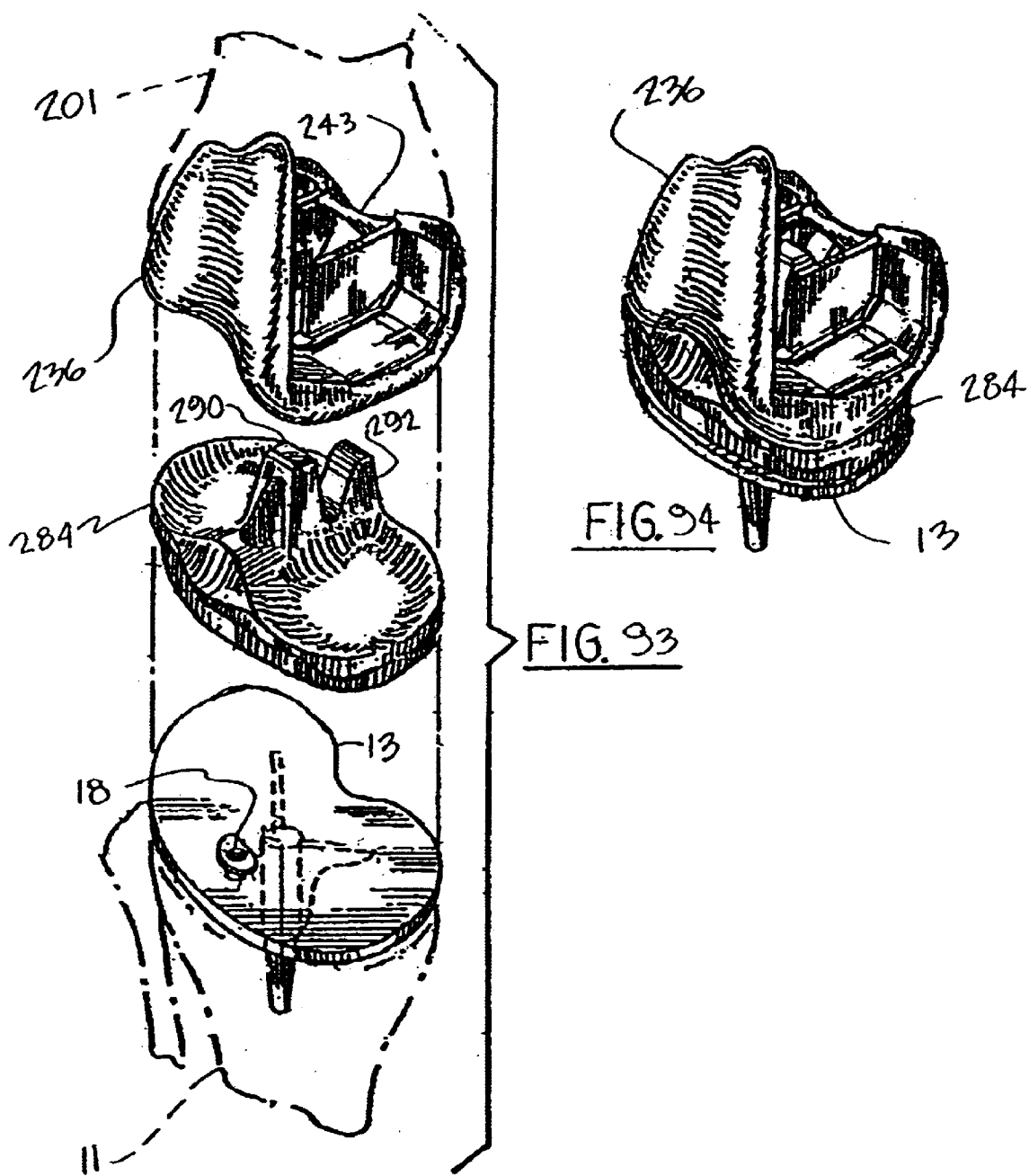

MOBILE BEARING KNEE PROSTHESIS

CROSS-REFERENCE TO RELATED APPLICATIONS

This is a continuation-in-part of U.S. patent application Ser. No. 09/670,186, filed Sep. 26, 2000, now U.S. Pat. No. 6,428,577 which is a continuation-in-part of U.S. patent application Ser. No. 09/082,179, filed May 20, 1998, now U.S. Pat. No. 6,123,728 which is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to orthopaedic prosthetic devices, and more particularly to an improved rotating platform, mobile knee prosthesis that incorporates anterior stabilization along with the ability to constrain the movement of the articular surface from rotation and translation, to rotation only.

2. General Background of the Invention

Femoral rollback is believed to improve range of motion and extensor mechanism leverage so as to improve efficiency and more accurately replicate natural kinematics. Conventional mobile bearing designs may Lack the desired effect of femoral rollback, particularly in the absence of the posterior cruciate ligament.

Posterior Stabilized (PS) fixed bearing designs provide femoral rollback by articulating a cam on the femoral component with a post on the tibial articular insert during flexion. However, PS fixed bearing designs do not have the advantages of mobile bearing designs with regards to enhanced range of motion, reduced rehabilitation time, improved patellofemoral alignment, increased contact area, and reduced bone-implant interface shear forces.

In fixed bearing designs, excessive wear of the PS post can occur during articulation with the femoral cam. Internal-external rotation of the femoral component reduces the PS post-femoral cam congruency which increases contact stresses. The increased contact stresses can lead to excessive polyethylene wear and component failure. Allowing the PS post to rotate within a fixed articular insert will maintain femoral cam-PS post congruency during internal/external rotation of the femoral component.

Further, in any type of posterior stabilized design (fixed bearing or mobile bearing), one of the most problematic failure modes of the polyethylene is the fracture of the central post of the insert. This failure can be attributed to "notching" the anterior side of the central post with the anterior most inner-condylar area of the femoral component. Thus, any mechanism to reduce the probability for impingement of the femoral component against the anterior side of the tibial central post in hyper-extension would reduce the probability for tibial insert post failure due to "notching" and ultimately breaking.

Previous rotating platform designs have incorporated rotating only, or rotation and translation through the use of different prostheses. An example of a prosthesis that rotates and translates is shown in British publication 2219942, entitled "Knee Prosthesis". U.S. Pat. No. 5,906,643 provides a tibial baseplate with a post that protrudes through a meniscal component and articulates with a cam on a femoral component. The post is an integral part of the tibial baseplate.

U.S. Pat. No. 5,879,392 provides a tibial baseplate with a fixed post that extrudes through the stem of the tibial baseplate and through the bearing component and articulates with a recess within the femoral component.

EP 0 916 321 A2 provides a femoral component with transverse flanges on the medial and lateral surfaces of the posterior stabilized box that articulate with projections from the medial and lateral surfaces of the post.

WO 95/35484 provides a bearing component with a post that articulates with a recess within the femoral component. The bearing component is limited in rotational, anterior, and posterior movement with respect to the tibial component.

The following patents relate to other orthopedic prosthetic devices, many of the listed patents pertaining to a knee prosthesis:

| Patent # | Issue Date | Title |
| --- | --- | --- |
| 3,899,796 | 08/19/75 | Metacarpophalangeal Joint |
| 4,016,606 | 04/12/77 | Knee Joint Prosthesis. |
| 4,094,017 | 06/13/78 | Knee Joint Prosthesis With Patellar-Femoral Contact |
| 4,216,549 | 08/12/80 | Semi-Stable Total Knee Prosthesis |
| 4,224,697 | 09/30/80 | Constrained Prosthetic Knee |
| 4,257,129 | 03/24/81 | Prosthetic Knee Joint Tibial Implant |
| 4,340,978 | 07/27/82 | New Jersey Meniscal Bearing Knee Replacement |
| 4,673,407 | 06/16/87 | Joint-Replacement Prosthetic Device |
| 4,822,366 | 04/18/89 | Modular Knee Prosthesis |
| 4,936,853 | 06/26/90 | Modular Knee Prosthesis |
| 4,950,297 | 08/21/90 | Knee Prosthesis |
| 4,959,071 | 09/25/90 | Partially Stabilized Knee Prosthesis |
| 5,007,933 | 04/16/91 | Modular Knee Prosthesis System |
| 5,032,132 | 07/16/91 | Glenoid Component |
| 5,071,438 | 12/10/91 | Tibial Prosthesis With Pivoting Articulating Surface |
| 5,116,375 | 05/26/92 | Knee Prosthesis |
| 5,271,747 | 12/21/93 | Meniscus Platform for an Artificial Knee Joint |
| 5,282,868 | 02/01/94 | Prosthetic Arrangement for a Complex Joint, Especially Knee Joint |
| 5,314,483 | 05/24/94 | Meniscus Platform for an Artificial Knee Joint |
| 5,344,460 | 09/06/94 | Prosthesis System |
| 5,370,699 | 12/06/94 | Modular Knee Joint Prosthesis |
| 5,387,240 | 02/07/95 | Floating Bearing Prosthetic Knee |
| 5,395,401 | 03/07/95 | Prosthetic Device for a Complex Joint |
| 5,404,398 | 04/11/95 | Prosthetic Knee With Posterior Stabilized Femoral Component |
| 5,413,604 | 05/09/95 | Prosthetic Knee Implant for an Anterior Cruciate Ligament Deficient Total Knee Replacement |
| 5,413,608 | 05/09/95 | Knee Joint Endoprosthesis for Replacing the Articular Surfaces of the Tibia |
| 5,549,686 | 08/27/96 | Knee Prosthesis Having a Tapered Cam |
| 5,609,639 | 03/11/97 | Prosthesis for Knee Replacement |
| 5,658,342 | 08/19/97 | Stabilized Prosthetic Knee |
| 5,702,466 | 12/30/97 | Rotational and Translational Bearing Combination in Biological Joint Replacement |
| 5,782,925 | 07/21/98 | Knee Implant Rotational Alignment Apparatus |
| 5,871,543 | 02/16/99 | Tibial Prosthesis With Mobile Bearing Member |

-continued

| Patent # | Issue Date | Title |
|---|---|---|
| 5,871,545 | 02/16/99 | Prosthetic Knee Joint Device |
| 5,879,394 | 03/09/99 | Tibial Element for a Replacement Knee Prosthesis |
| 5,906,643 | 05/25/99 | Stabilized Mobile Bearing Knee |
| 5,928,286 | 07/27/99 | Tibial Element for a Replacement Knee Prosthesis |
| 5,935,173 | 08/10/99 | Knee Prosthesis |
| 6,039,764 | 03/21/00 | Prosthetic Knee With Adjusted Center of International/External Rotation |
| 6,099,570 | 08/08/00 | Knee Joint Prothesis |
| 6,165,223 | 12/26/00 | Floating Bearing Knee Joint Prosthesis With a Fixed Tibial Post |
| 6,210,444 | 04/03/01 | Tibial Knee Component With a Mobile Bearing |
| 6,217,618 | 04/17/01 | Tibial Knee Component With a Mobile Bearing |
| 6,238,434 | 05/29/01 | Knee Joint Prosthesis With Spinout Prevention |

GENERAL DISCUSSION OF THE PRESENT INVENTION

The present invention has as an object a tibial prosthesis and mating articular insert with specially configured stabilization posts. The invention enables for the surgeon to convert a mobile bearing articular surface from a fixed to a rotating only or translating only. The prosthesis can also provide both rotation and translation simultaneously.

These conversions are accomplished with special locking members or plugs that connect to the tibial base special plate. The plugs can be secured to the base plate with a taper lock or a threaded connection for example.

A post on the proximal tibial base plate can be positioned with an offset with respect to an oval hole in the articular insert to provide anterior stabilization in the total knee prosthesis.

The prosthesis of the present invention will be used as part of a total knee surgery when the surgeon chooses to use a prosthesis that incorporates a particular, selected relative motion between tibial tray and tibial insert.

This present invention consists of a posterior stabilized "PS" post which is secured to the mobile bearing tibial baseplate allowing only rotational movement. The PS post captures a bearing component to the tibial baseplate through an elongated slot in the bearing component. The elongated slot in the bearing component allows it to translate anteriorly and posteriorly with respect to the posterior stabilized post. The bearing component may also rotate with respect to the tibial baseplate in conjunction with the PS post. The bearing component has two concave surfaces that are articulate with the convex surfaces of the femoral component, and that are roughly congruent with the convex surfaces of the femoral component at zero degrees of flexion or full extension. The PS post articulates with a recess or cam of the femoral component to provide femoral rollback.

In addition to the above described design, the PS post should allow for posterior translation, in addition to rotational movement. This posterior movement would allow the post to translate instead of impinging upon the innercondylar notch area of the femoral component in hyperextension.

The PS post has a flat distal surface that articulates with the tibial baseplate. A T-slot is located on the distal end and-articulates with a T-post on the tibial baseplate. A through hole in the PS post is located such that a rotation peg can capture the PS post to the tibial baseplate while the T-slot of the PS post is engaged with the T-post of the tibial baseplate. The rotation peg allows only rotational freedom of the PS post with respect to is the tibial baseplate. The PS post has a flange on the medial and lateral surfaces that capture the bearing component through a counterbore on the medial and lateral sides of an elongated slot of the bearing component. The elongated slot of the bearing component is larger than the PS post in the anterior-posterior direction such that the bearing component has limited translation with respect to the PS post. The bearing component may also rotate with respect to the tibial baseplate in conjunction with the PS post. The bearing component has two concave surfaces that are congruent to the convex surfaces of the femoral component. A cam mechanism on the femoral component can be a concave cylinder that can be congruent to the convex posterior surface of the PS post. The internal/external rotation of the PS post with the femoral component can maintain this congruency throughout the range of motion unlike designs with a fixed PS post.

The addition of the posterior translation can occur with an anterior to posterior "A/P" slot instead of a hole as seen in the inferior view above. This slot would allow for posterior translation of the post relative to the insert/baseplate.

The "PS" post may engage the tibial baseplate through a pin means or through a boss of a configuration other than a T-post. The "PS" post may secure the bearing component through the use of slots or other means of capture. The "PS" post may articulate with a closed recess within the femoral component rather than a cam mechanism.

With the fixed bearing design, the means of "PS" post capture may be with the use of a retaining ring or a cross pin. The PS post may not require capture with the fixed bearing articular insert.

The present invention also provides an improved knee prosthesis apparatus that includes a tibial prosthesis that is configured to be surgically implanted on a patient's transversely cut proximal tibia and a femoral component. The femoral component articulate with a tibial insert having a proximal surface that engages the femoral component, the insert having a distal surface that fits against and articulates with the proximal surface of the tibial prosthesis.

A constraining mechanism joins the tibial insert to the tibial prosthesis in a selective fashion that enables a number of different possible relative motions between the insert and the tibial prosthesis, including anterior to posterior translation with rotation, or rotation only.

All or part of the constraining mechanism is separable from the tibial prosthesis, and selective removal of all or part of the constraining mechanism determines which of the said possible relative motions will take place.

The tibial prosthesis can have a fixator for holding the tibial prosthesis on a patient's proximal tibia such as for example, a stem, spike, cement, etc.

The proximal surface of the insert can have one or more concavities for articulating with the femoral component.

The femoral component can include an intercondylar surface that is positioned to contact the post, enabling relative motion between the femoral component and the insert to be constrained.

An additional embodiment of the apparatus of the present invention provides a cam and bar arrangement that prevents "spin out" that can occur in mobile bearing tibia designs. In mobile bearing tibia designs, the tibial component is free to rotate relative to the femur. In one embodiment, the femoral component is provided with a transverse, specially shaped bar that cooperates with a tibia cam provided on the tibial insert. This improved arrangement forces a "roll back" of the femoral component relative to the tibial component in flexion. The tibial component insert provides a pair of projecting portions, including a centrally located post having a posterior tibia cam surface and a posterior projecting portion that has a convex anterior surface. In between these two projecting portions, a slot is provided having a specially shaped bottom portion that "captures" the transverse bar of the femoral component, constraining the bar and thus the femoral component. This apparatus disallows the tibia from spinning, eliminating any spin out condition.

BRIEF DESCRIPTION OF THE-SEVERAL VIEW OF THE DRAWINGS

For a further understanding of the nature, objects, and advantages of the present invention, reference should be had to the following detailed description, read in conjunction with the following drawings, wherein like reference numerals denote like elements and wherein:

FIG. 5 is a rear, elevational and exploded view of the preferred embodiment of the apparatus of the present invention illustrating the articular polymeric insert and tray portions thereof;

FIG. 6 is a sectional, elevational view of the preferred embodiment of the apparatus of the present invention shown with the locking member removed;

FIG. 7 is another sectional, elevational view of the preferred embodiment of the apparatus of the present invention illustrating the locking member in operating position when only rotational movement is desired;

FIG. 8 is a partial top view of the preferred embodiment of the apparatus of the present invention showing the polymeric insert;

FIG. 9 is a partial, bottom view of the preferred embodiment of the apparatus of the present invention showing the polymeric insert;

FIG. 10 is a partial rear view of the preferred embodiment of the apparatus of the present invention showing the polymeric insert;

FIG. 11 is a partial sectional view of the preferred embodiment of the apparatus of the present invention taken along lines 11—11 of FIG. 8;

FIG. 12 is a sectional view of the preferred embodiment of the apparatus of the present invention taken along lines 12—12 of FIG. 8;

FIG. 44 is a bottom view of the tray portion of the third alternate embodiment of the apparatus of the present invention;

FIG. 45 is a side view of the tray portion of the third alternate embodiment of the apparatus of the present invention;

FIG. 46 is a perspective view of the tray portion of the third alternate embodiment of the apparatus of the present invention;

FIG. 47 is a posterior view of the tray portion of the third alternate embodiment of the apparatus of the present invention;

FIGS. 48–49 are fragmentary views of the third alternate embodiment of the apparatus of the present invention illustrating one of the plug portions thereof; and FIGS. 50–51 are side and top views of a second plug portion that is used with the third alternate embodiment of the apparatus of the present invention;

FIG. 52 is a perspective, exploded view of a fourth alternative embodiment of the apparatus of the present invention;

FIG. 53 is a sectional, elevational view of the fourth alternative embodiment shown in FIG. 52, shown with the locking member removed;

FIG. 54 is another sectional, elevational view of the fourth alternative embodiment shown in FIG. 52, illustrating the locking member in operating position when only rotational movement is desired;

FIG. 60 is a side elevation view of the fifth alternate embodiment of the apparatus of the present invention showing the knee in an extended position;

FIG. 61 is a side elevation view of the fifth alternate embodiment of the apparatus of the present invention showing the knee in a flexed position;

FIG. 82 is a schematic elevation view of a seventh embodiment of the apparatus of the present invention, in knee extension position;

FIG. 83 is another schematic elevation view of the seventh embodiment of the apparatus of the present invention, showing the knee in 90 degree flexion;

FIG. 84 is a top fragmentary view of the seventh embodiment of the apparatus of the present invention illustrating the insert portion thereof;

FIG. 85 is a fragmentary elevation view of the seventh embodiment of the apparatus of the present invention illustrating the insert portion thereof;

FIG. 86 is a side fragmentary elevation view of the seventh embodiment of the apparatus of the present invention showing the insert portion thereof;

FIG. 87 is a fragmentary perspective view of the seventh embodiment of the apparatus of the present invention showing the insert portion thereof;

FIG. 88 is a fragmentary perspective view of the seventh embodiment of the apparatus of the present invention showing the tray portion thereof;

FIG. 89 is a partial plan view of the seventh embodiment of the apparatus of the present invention showing the femoral component portion thereof;

FIG. 90 is a frontal, anterior view of the femoral component shown in FIG. 89;

FIG. 91 is a side view taken along lines 91—91 of FIG. 90;

FIG. 92 is a fragmentary perspective view of the seventh embodiment of the apparatus of the present invention illustrating the femoral component portion thereof;

FIG. 93 is an exploded perspective view of the seventh embodiment of the apparatus of the present invention; and FIG. 94 is a perspective view of the seventh embodiment of the apparatus of the present invention.

DETAILED DESCRIPTION OF THE INVENTION

Figure 1:
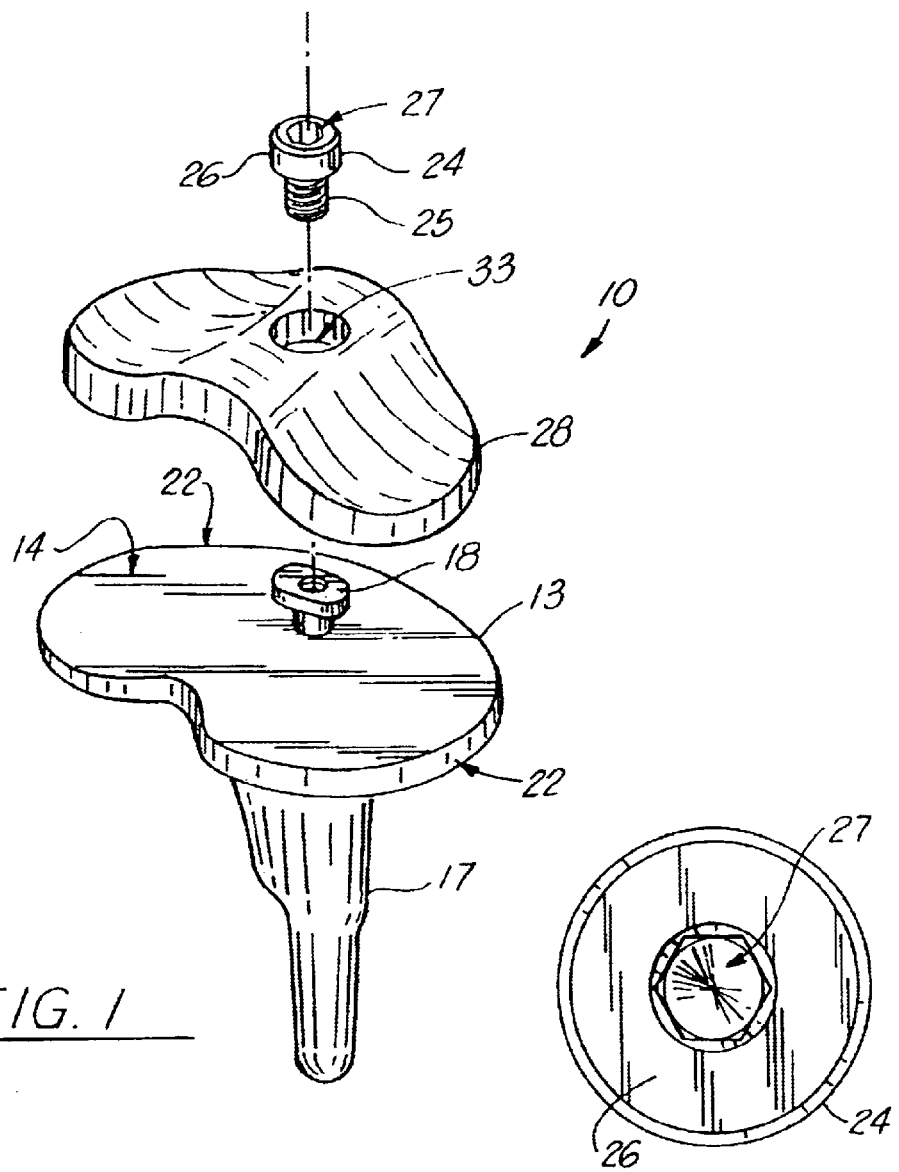
FIG. 1 is a perspective, exploded view of the preferred embodiment of the apparatus of the present invention.
Figure 3:
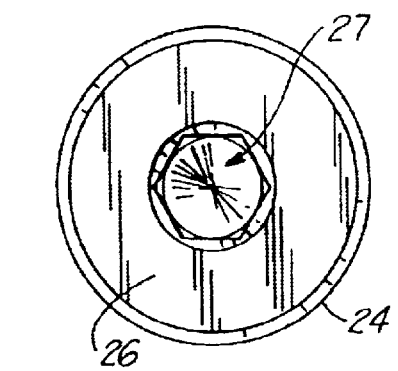
FIG. 3 is a top, fragmentary view of the preferred embodiment of the apparatus of the present invention illustrating the locking member portion thereof.
Figure 2:
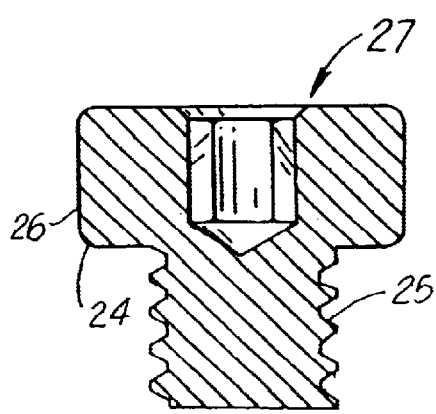
FIG. 2 is a partial sectional of the preferred embodiment of the apparatus of the present invention illustrating the locking member portion thereof.
Figure 4:
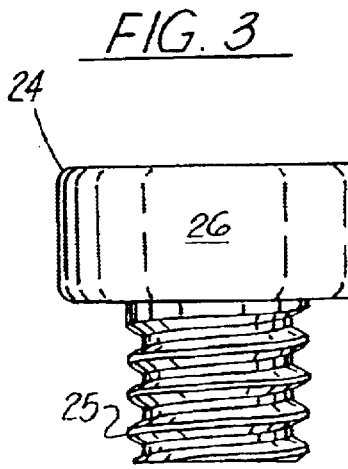
FIG. 4 is a partial, elevational view of the preferred embodiment of the apparatus of the present invention illustrating the locking member portion thereof.

FIGS. 1–7 show generally the preferred embodiment of the apparatus of the present invention designated generally by the numeral 10 in FIGS. 1, 6, and 7.

Mobile bearing knee prosthesis 10 is placed upon a patient's surgically cut proximal tibia 11 at a surgically cut proximal surface 12 that is preferably flat. This enables a tray 13 to be mounted to the proximal tibia 11 at surface 12 as shown in FIGS. 6 and 7. Tray 13 has a flat proximal surface 14 and a generally flat distal surface 15 that mates with and faces the surgically prepared surface 12 as shown in FIGS. 6–7. The tray 13 can provide a plurality of spikes 16 and a stern 17 for enhancing implantation to the patient's proximal tibia 11. However, any other known attachment can be used to affix tray 3 to a patient's proximal tibia such as chemical (eg. element) or mechanical fasteners (or fastener).

Figure 13:
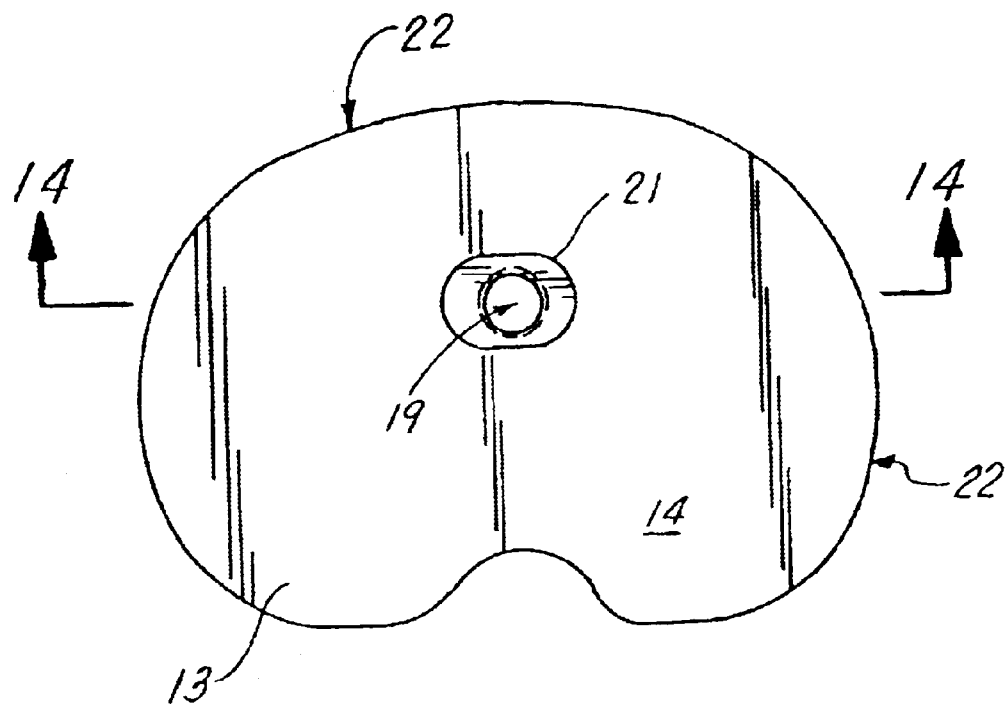
FIG. 13 is a partial top view of the preferred embodiment of the apparatus of the present invention illustrating the tray or baseplate.
Figure 14:
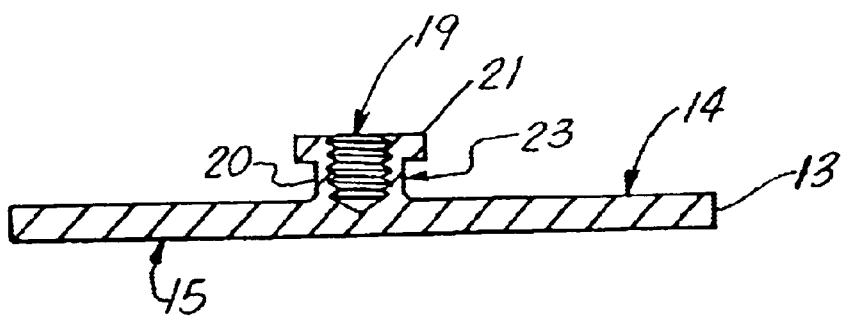
FIG. 14 is a sectional view of the preferred embodiment of the apparatus of the present invention taken along lines 14—14 of FIG. 13.

The proximal surface 14 of tray 13 provides a post 18 having an internally threaded socket 19. Post 18 is comprised of a generally cylindrically-shaped smaller diameter section 20 and an enlarged flange 21 that mounts to the top of cylindrically-shaped 20 as shown in FIGS. 5 and 13–14. Tray 13 has a periphery 22. A recess 23 is provided in between the proximal surface 14 of tray 13 and flange 21.

A locking member 24 forms a removable connection with the socket 19. Locking member 24 has an externally cylindrical section 25 that provides threads that correspond to the threads of internally threaded socket 19 so that the locking member 24 can be threaded into the socket 19 as shown in FIG. 7. Locking member 24 includes an enlarged cylindrically-shaped head 26 having a tool receptive socket 27 such as a hexagonal socket for example.

An insert 28 provides a vertical channel 33 that can be placed in communication with post 18 as shown in FIGS. 6 and 7. Insert 28 provides a preferably flat distal surface 29 that communicates with the flat proximal surface 14 of tray 13. A pair of spaced apart concavities 30, 31, are provided for defining articulation surfaces that cooperate with correspondingly shaped articulating surface on a patient's femur or femoral implant. The insert 28 has a periphery 32 that generally corresponds in shape to the periphery 22 of tray 13. Insert 28 can be polymeric or metallic or of a composite construction, such as metallic with a polymeric articulating surface(s) or polymeric with a metallic articulation surface (s).

Vertical channel 33 is comprised of a number of sections that are specially shaped to interact with the post 18 and locking member 24. Vertical channel 33 thus includes a proximal, cylindrically-shaped section 34, an oval shaped slot 35, and a distal opening 36. The distal opening 36 includes a generally oval section 37 and a somewhat half oval section 38. The oval section 38 can track any of three directions including a pure anterior to posterior direction, a direction that is at an angle to a pure anterior to posterior direction; or a direction that is an arcuate or curved path that pivots or rates about a point that is not located along the A/P centerline of the insert. Flat surfaces 39, 40 are positioned at the top of and at the bottom of the oval shaped slot 35 as best seen in FIGS. 8–11. The cylindrically-shaped head 26 of locking member 24 closely fits the cylindrically-shaped section 36.

In order to assemble insert 28 to tray 13, the distal surface of 29 of insert 28 is placed next to and generally parallel to the proximal surface 14 of tray 13. Post 18 is aligned with vertical channel 33 of insert 28. During assembly of insert 28 to tray 13, the post 18 is shaped to enter the oval opening portion 37 of distal opening 36. Once the distal surface 29 of insert 28 meets proximal surface 14 of tray 13, flange 21 aligns with oval shaped slot 35 of vertical channel 33. After such assembly, insert 28 is held in position by post 18. This retention of insert 28 by post 18 occurs when flange 21 engages flat surface 40 to prevent separation if any rotation (see arrow 41 of FIG. 17) at all occurs between insert 28 and tray 13. If no rotation has occurred between insert 28 and tray 13 (see FIG. 15), the oval shaped circular section 37 is sized to allow post 18 to be inserted into or withdrawn from channel 33.

Figure 15:
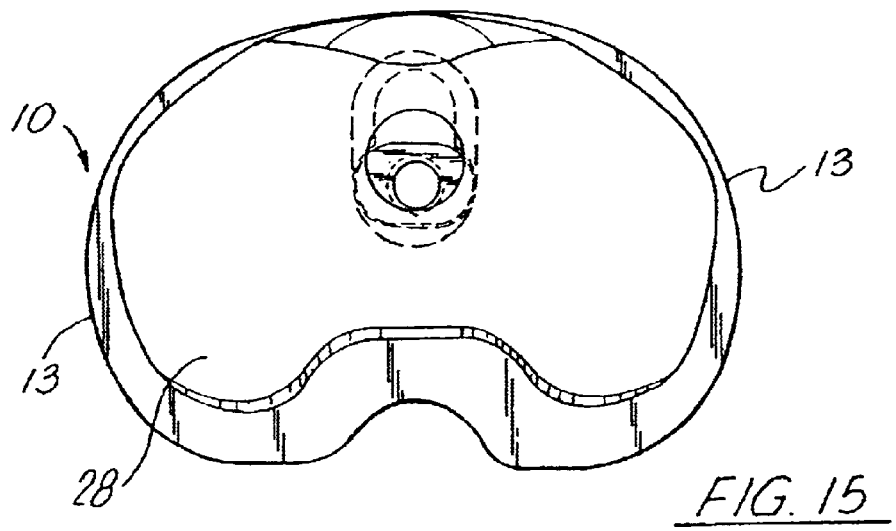
FIG. 15 is a top view of the preferred embodiment of the apparatus of the present invention illustrating the insert and tray portions thereof in operating position without the locking member.
Figure 16:
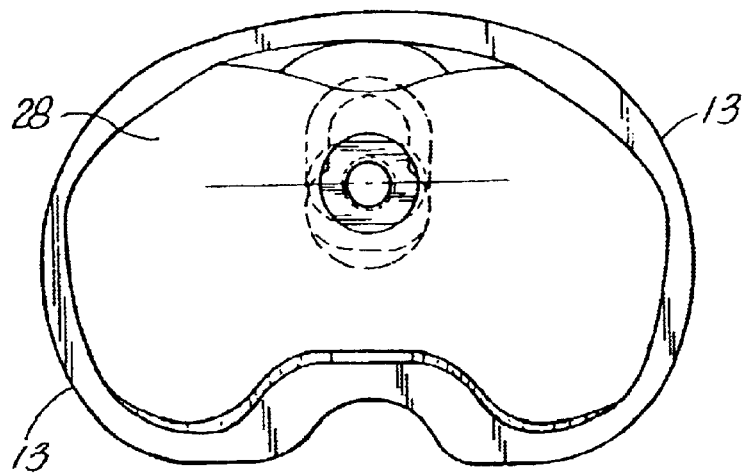
FIG. 16 is a top side. view of the preferred embodiment of the apparatus of the present invention illustrating the insert, tray and locking member portions thereof in operating position.
Figure 17:
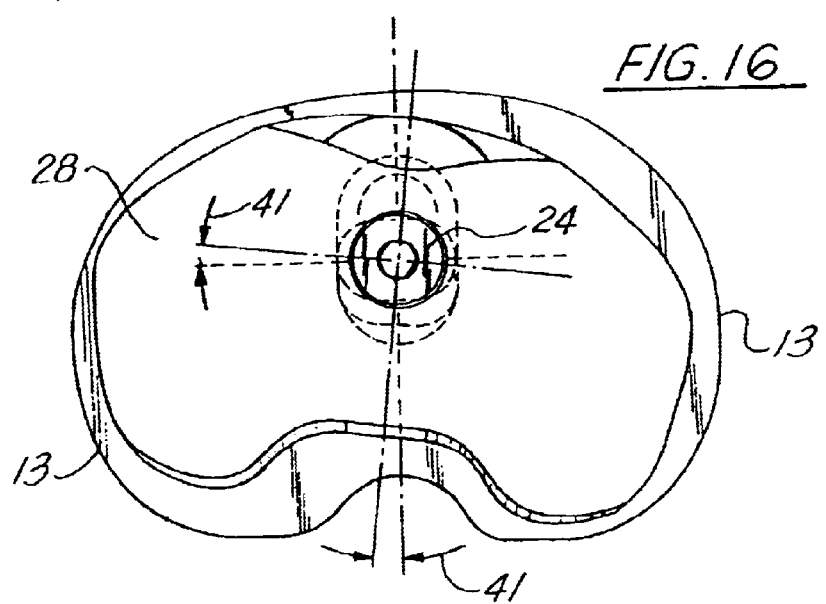
FIG. 17 is a top view of the preferred embodiment of the apparatus of the present invention illustrating rotation of the insert relative to the tray.

In FIG. 15, the apparatus 10 is shown in an assembled position wherein the fastener 24 has been removed so that the insert 28 can move in a translation and rotation and rotation fashion relative to tray 13. In FIG. 16, the fastener 24 has been threadably attached to the internally threaded socket 19 and is in operating position. In FIG. 17, the insert 28 can rotate relative to the tray 13 through an angle 41. However, because of the attachment of fastener 24, only rotation and not translation is permitted in FIG. 17. Thus, in FIG. 17, the apparatus 10 of the present invention provides a mating mechanism between the post 18 and the fastener 24 and the insert 28 that defines a constraining mechanism so that the insert 28 may be constrained for rotation only relative to the tray 13.

In FIGS. 18–21 and 22–25, there is seen various alternate constructions of the post that can be used instead of post 18 when the selected post is fitted to the tibial tray 13. In FIGS. 22–25, an alternate construction of the insert 28 is shown with an illustration of the various types of relative motion between the insert and the tibial tray that can be selectively provided to a surgeon.

Figure 18:
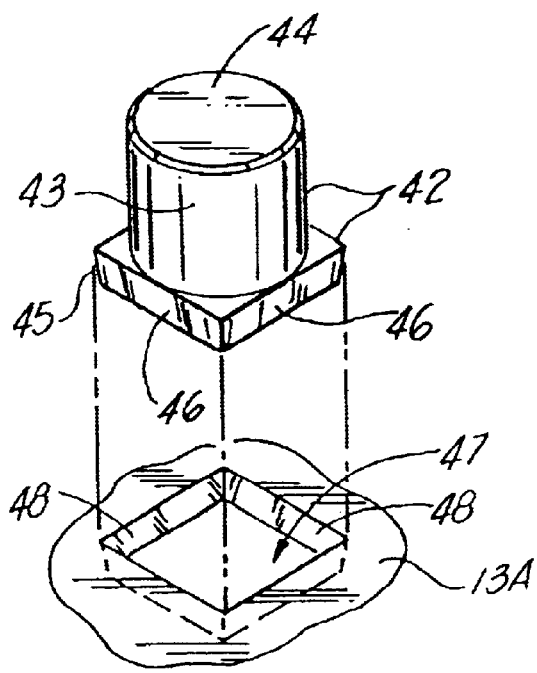
FIGS. 18–21 are fragmentary perspective views of an alternate embodiment of the apparatus of the present invention illustrating constructions for the post portion and illustrating the connection between the post and the tray.

In FIGS. 18–21, four different constructions of the post are provided. In FIG. 18, a post 42 has a cylindrical outer surface 43 and a circular top 44. Post 42 has a rectangular base 45 with a generally flat undersurface and a plurality of four inclined surfaces 46 which provides a means of attaching the post to the tray or the post may be permanently attached to the tray. The rectangular base 45 fits tray 13A socket 47 at its inclined surfaces 48 with a taper lock type connection for example. Other types, of connections could be used to join post 42 to tray 13A at socket 47.

Figure 19:
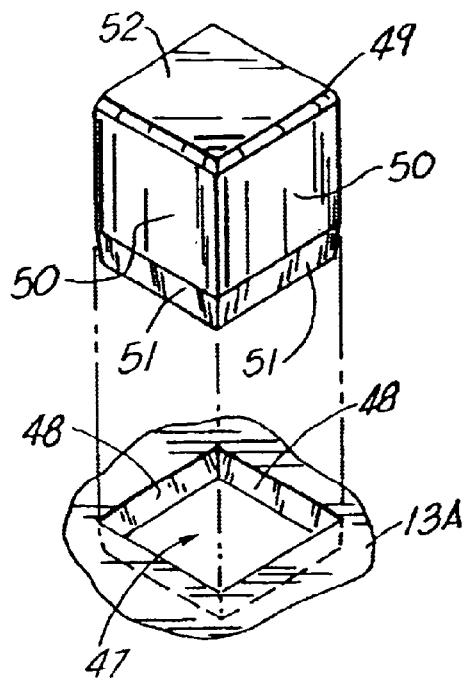

In FIG. 19, post 49 includes a plurality of four vertical side walls 50 and a plurality of four inclined surfaces 51. A rectangular flat top 52 is provided opposite a generally flat undersurface of post 49. The inclined surfaces 51 of post 49 fit similarly configured inclined surfaces 48 of socket 47 in tray 13A.

Figure 20:
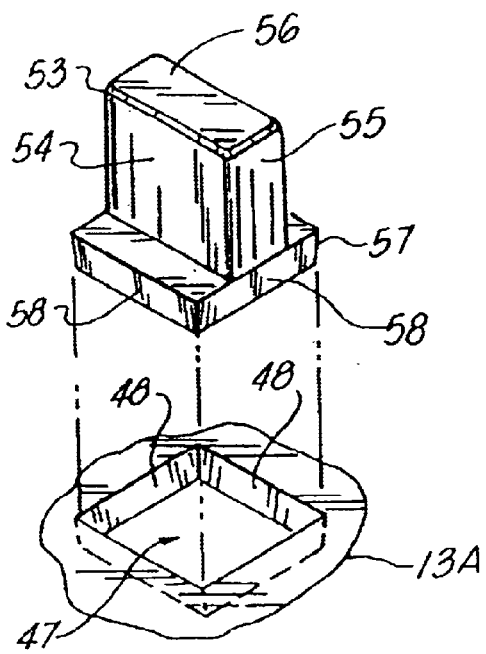

In FIG. 20, post 53 is generally rectangularly shaped providing a pair of opposed flat larger vertical side walls 54 and a pair of opposed flat smaller end walls 55 with a flat top 56. Post 53 has a base 57 that includes four inclined surfaces 58. The inclined surfaces 58 form a taper lock connection with four similarly configured inclined surfaces 48 of socket 47 of tray 13A.

Figure 21:
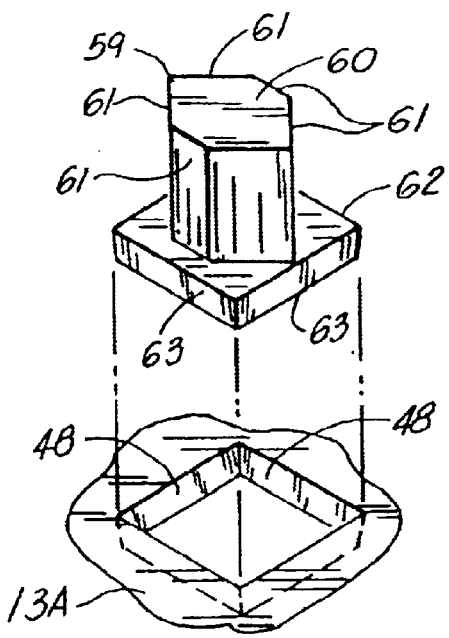

In FIG. 21, post 59 has a hexagonal shape providing a hexagonally shaped flat top 60. Hexagonal post 59 also has a plurality of vertical side walls 61 and a rectangular base 62. The base 62 has inclined surfaces 63 that form a taper lock connection with inclined surfaces 48 of tray socket 47 of tray 13A.

Figure 22:
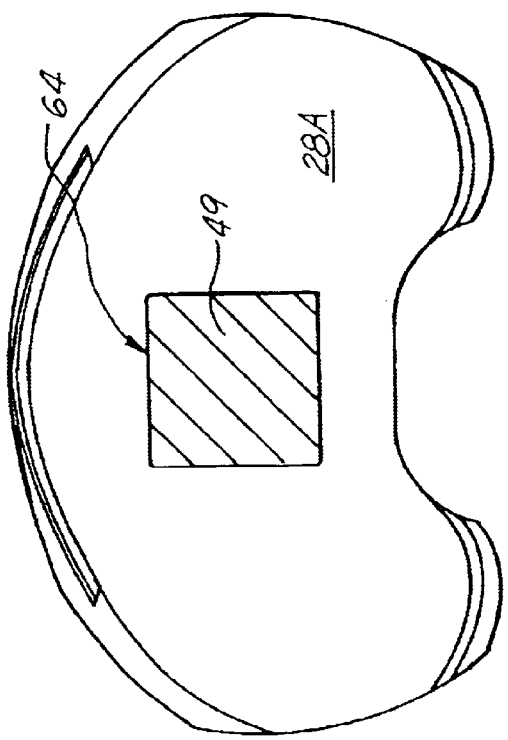
FIGS. 22–25 are schematic plan views of alternate constructions of the tibial insert to be used respectively with the post constructions of FIGS. 18–21.
Figure 23:
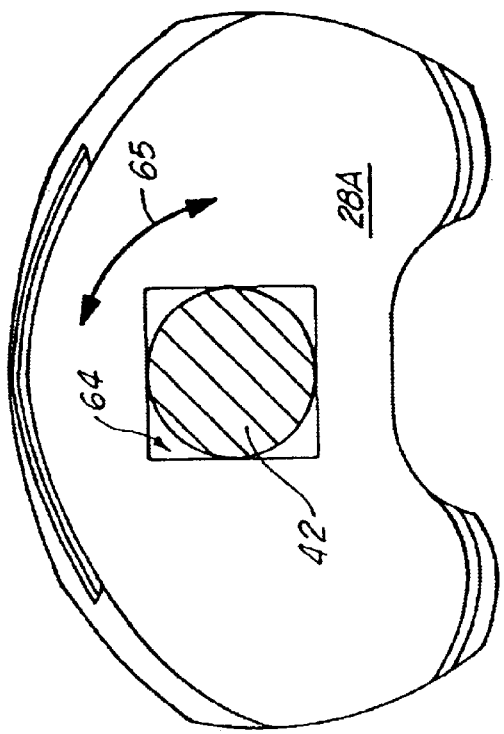

In FIG. 22, insert 28A provides a square opening 64 that exactly fits peg 49. In FIG. 22, there is no relative motion between insert 28A and tray 13A. In FIG. 23, rotational motion only is indicated by arrow 65 between insert 28A and tray 13A when peg 42 is used.

Figure 24:
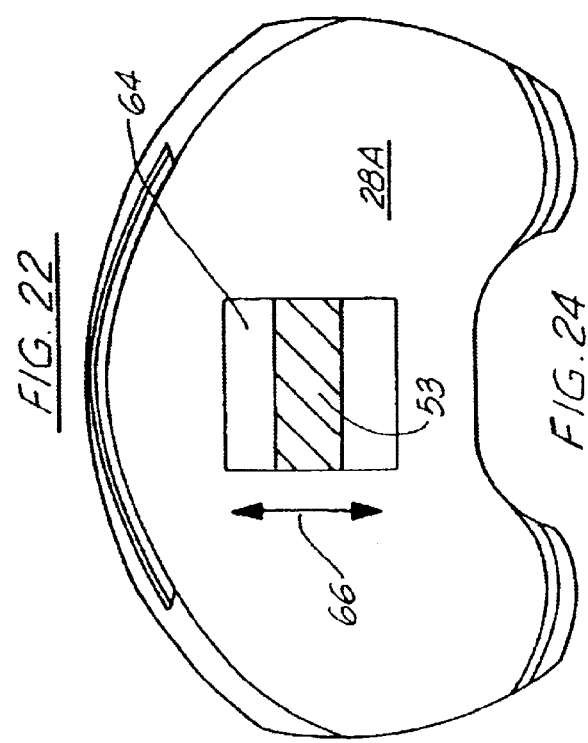
Figure 25:
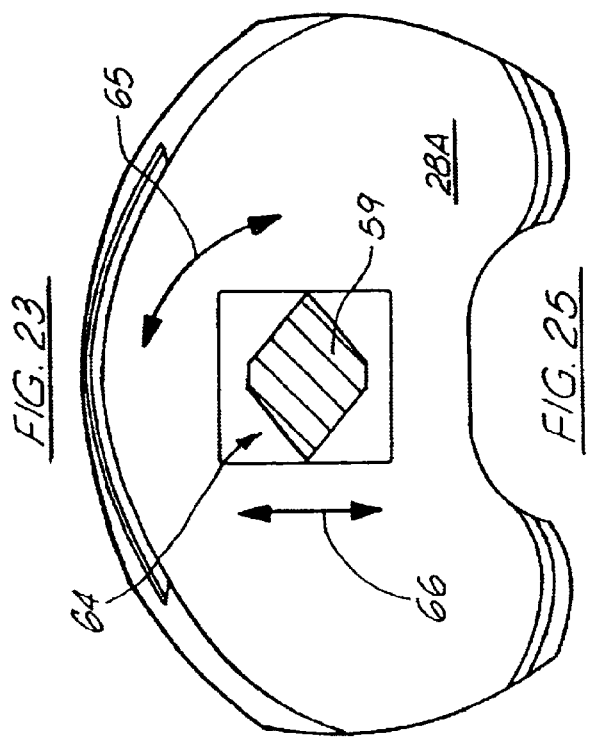

In FIG. 24, the rectangular peg 53 enables only translational movement between the insert 28A and tray 13A as indicated by arrow 66. In FIG. 25, the hexagonal peg 59 enables both rotational motion as indicated by arrow 65 and translational motion as indicated by arrow 66 between insert 28A and tray 13A.

Figure 37:
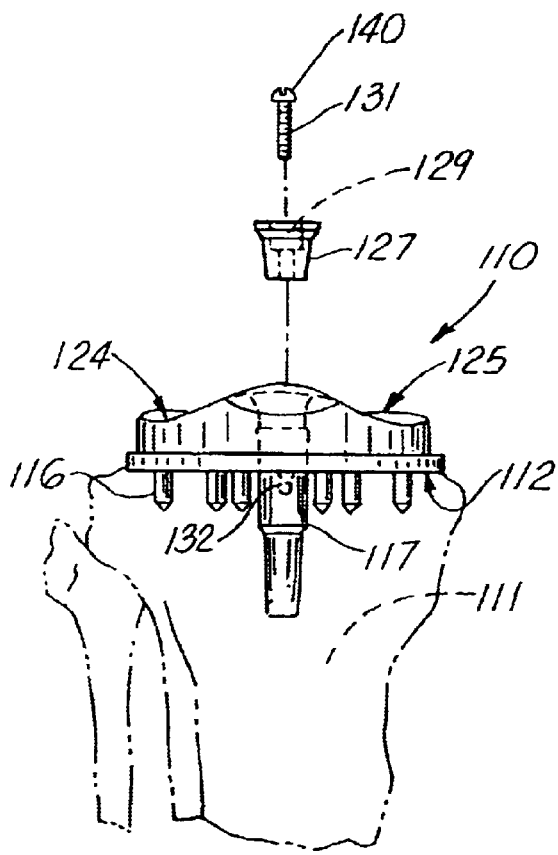
FIG. 37 is an elevational view of the second alternate embodiment of the apparatus of the present invention illustrating the cap and set screw separated from the insert and tray portions thereof.

An alternate embodiment of mobile bearing knee apparatus 110 is shown generally in FIG. 37. In FIG. 37, the prosthesis 110 is shown positioned upon a patient's proximal tibia 111, specifically upon a flat surgically cut proximal surface 112 as shown.

Figure 26:
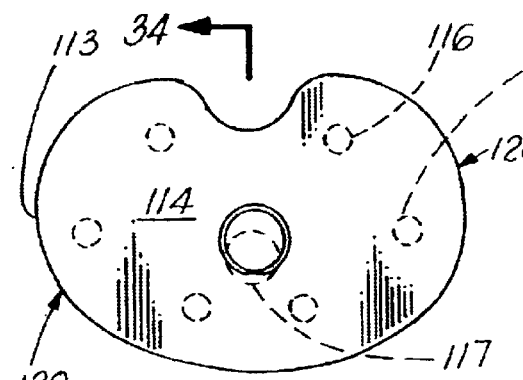
FIG. 26 is a top view of the second alternate embodiment of the apparatus of the present invention illustrating the tray portion thereof.
Figure 27:
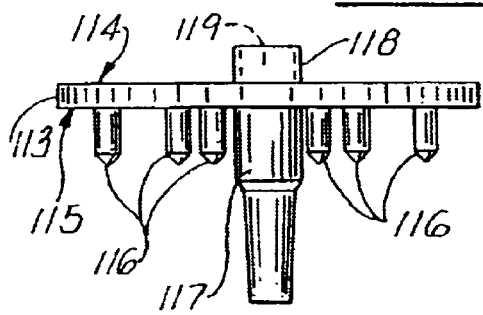
FIG. 27 is an elevational view of the second alternate embodiment of the apparatus of the present invention illustrating the tray portion thereof.
Figure 28:
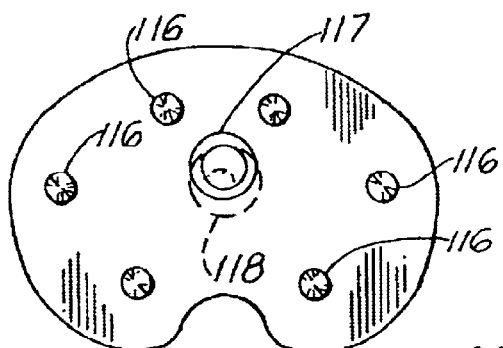
FIG. 28 is a bottom view of the second alternate embodiment of the apparatus of the present invention illustrating the tray portion thereof.

In FIGS. 26–28, tibial tray 13 is shown, which can be of metallic construction such as titanium alloy, for example. Tray 113 has a flat proximal surface 114 and a flat distal surface 115. A plurality of mechanical fasteners such as spikes 116 on surface 115 can be used to enhance fixation of tibial tray 113 to the patient's proximal tibial 111. Chemical fasteners (eg. cement) can also be used for fixation. A stem 117 can also be used to facilitate attachment of prosthesis 110 to the patient's tibia 111 at the tibial intramedullary canal.

The flat proximal surface 114 of tray 113 has a round post 118 with a hollow bore or socket 119. The post 118 is spaced inwardly from the periphery 120 of tray 113 as shown in FIGS. 26 and 27. The post 118 is preferably positioned with an offset with respect to oval slot 126 in the articular insert to provide anterior stabilization in the total knee prosthesis.

Figure 29:
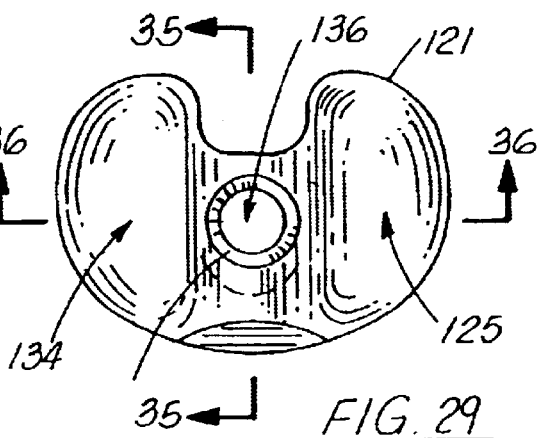
FIG. 29 is a plan view of the second embodiment of the apparatus of the present invention illustrating the polymeric insert portion thereof.
Figure 30:
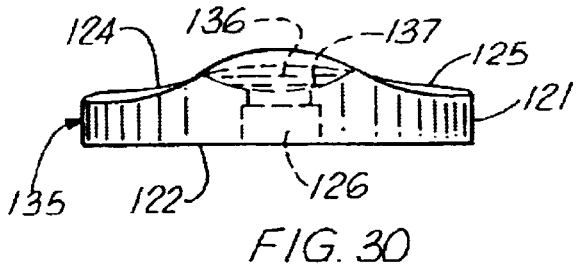
FIG. 30 is a frontal elevational view of the second alternate embodiment of the apparatus of the present invention illustrating the plastic insert portion thereof.
Figure 31:
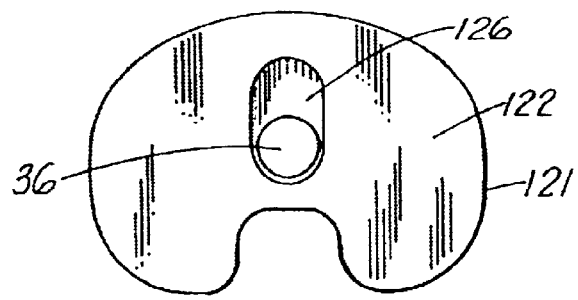
FIG. 31 is a bottom view of the plastic insert portion of the second alternate embodiment of the apparatus of the present invention.

FIGS. 29–31 show the insert 121 portion of the present invention, typically a polymeric plastic insert that fits tray 113. Insert 121 has a flat distal surface 122 and a proximal surface 123 that includes curved portions. These curved portions are in the form of concavities 124, 125 receive shaped surfaces of a femoral prosthesis after total knee joint replacement surgery is completed. The flat distal surface 122 of insert 121 has an anterior to posterior extending generally oval shaped slot 126 as shown in FIG. 31.

The slot 126 receives post 118 during use, enabling the insert 121 to slide in an anterior to posterior direction relative to tray 113.

The present invention provides a rotating platform, mobile knee prosthesis 110 that incorporates anterior stabilization along with the ability to selectively constrain the movement of the articular surface from rotation and translation to rotation only. This is accomplished by using an opening 136 in insert 121 that communicates with slot 126 as shown in FIGS. 29–31 and 35–38. The opening includes a frustoconical portion 137 that corresponds in shape to a similar frustoconical-shaped enlarged annular surface 134 of locking plug member 127. The locking plug member 127 is shown more particularly in FIGS. 32, 33, and 37.

Figures 32, 33:
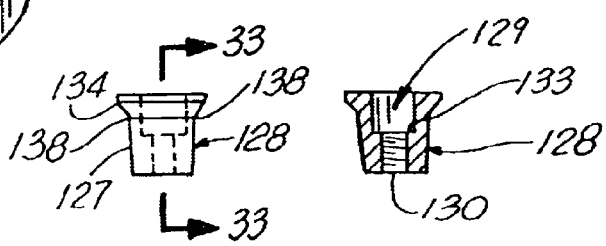
FIG. 32 is a fragmentary view of the second alternate embodiment illustrating the locking plug member portion thereof.
FIG. 33 is a sectional view taken along lines 33—33 of FIG. 32.
Figure 34:
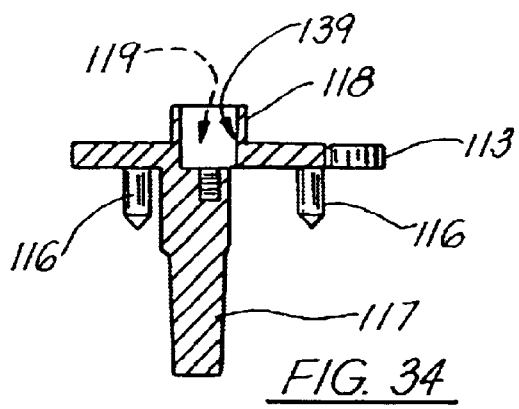
FIG. 34 is a sectional view taken along lines 34—34 of FIG. 26
Figure 35:
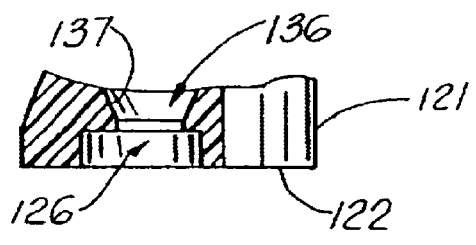
FIG. 35 is a sectional view taken along lines 35—35 of FIG. 29.
Figure 36:
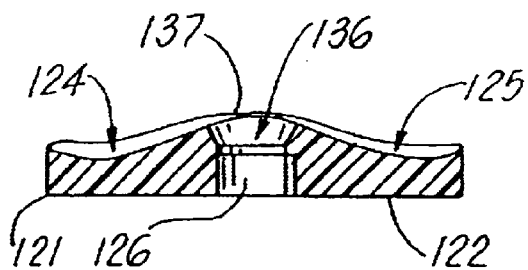
FIG. 36 is a sectional view taken along lines 36—36 of FIG. 29.

Locking plug member 127 includes a lower frustoconical surface 128. The frustoconical outer surface 128 of locking member 127 below annular reference line 138 is sized and shaped to fit and form a taper lock connection with surface 139 of frustoconical socket 119 of post 118. Above annular reference line 138, the enlarged annular shoulder has a frustoconical shape as shown in FIG. 32 that corresponds generally to the size and shape of frustoconical portion 137 of opening 136 as shown in FIG. 36.

When the locking member 127 is first placed through opening 136 of insert 121. and then into frustoconical socket 119, of post 118, a locking connection is formed between the frustoconical outer surface 128 of locking member 127 and the frustoconical surface 139 of post 118. This connection can be a taper lock type connection.

Locking screw 131 can be used to engage a correspondingly sized and shaped internally threaded opening 132 of tray 113 if desired. The locking screw 131 can include a head 140 that is enlarged so that the head 140 is retained by annular shoulder 133 of locking member 137 as shown in FIGS. 33 and 37.

Figure 38:
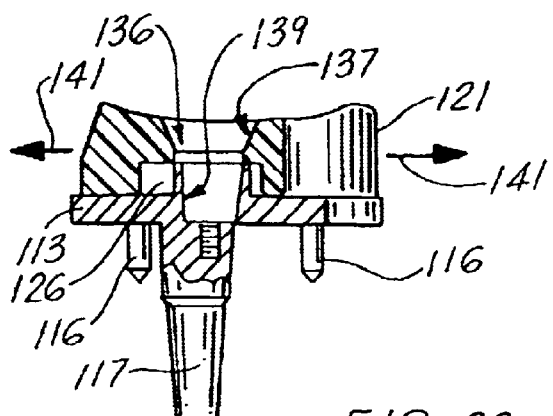
FIG. 38 is a partial sectional elevational view of the second alternate embodiment of the apparatus of. the present invention. illustrating the mobile insert moving with respect to the tray.

In FIG. 38, arrows 141 indicate sliding movement of insert 121 relative to tray 113 as occurs when locking plug member 127 is removed. In such a situation, the insert 121 is free to slide with respect to tray 113. The distal surface 122 of insert 121 slides upon the flat proximal surface 114 of tray 113. Post 118 slides relative to slot 126.

When locking member 127 is inserted through opening 136 and into socket 119 of post 118, sliding movement is prevented. The enlarged annular shoulder 134 of locking member 127 engages the frustoconical portion 137 of opening 136 disallowing a sliding action of insert 121 relative to tray 113. However, the enlarged annular shoulder 134 of locking member 127 is slightly spaced from frustoconical portion 137 of opening 136, so that rotational movement of insert 121 relative to tray 113 is permitted. The second alternate embodiment of the present invention provides a rotating platform, mobile knee prosthesis 110 that incorporates anterior stabilization along with the ability to constrain movement of the articular surface from rotation and translation to rotation only.

Figure 39:
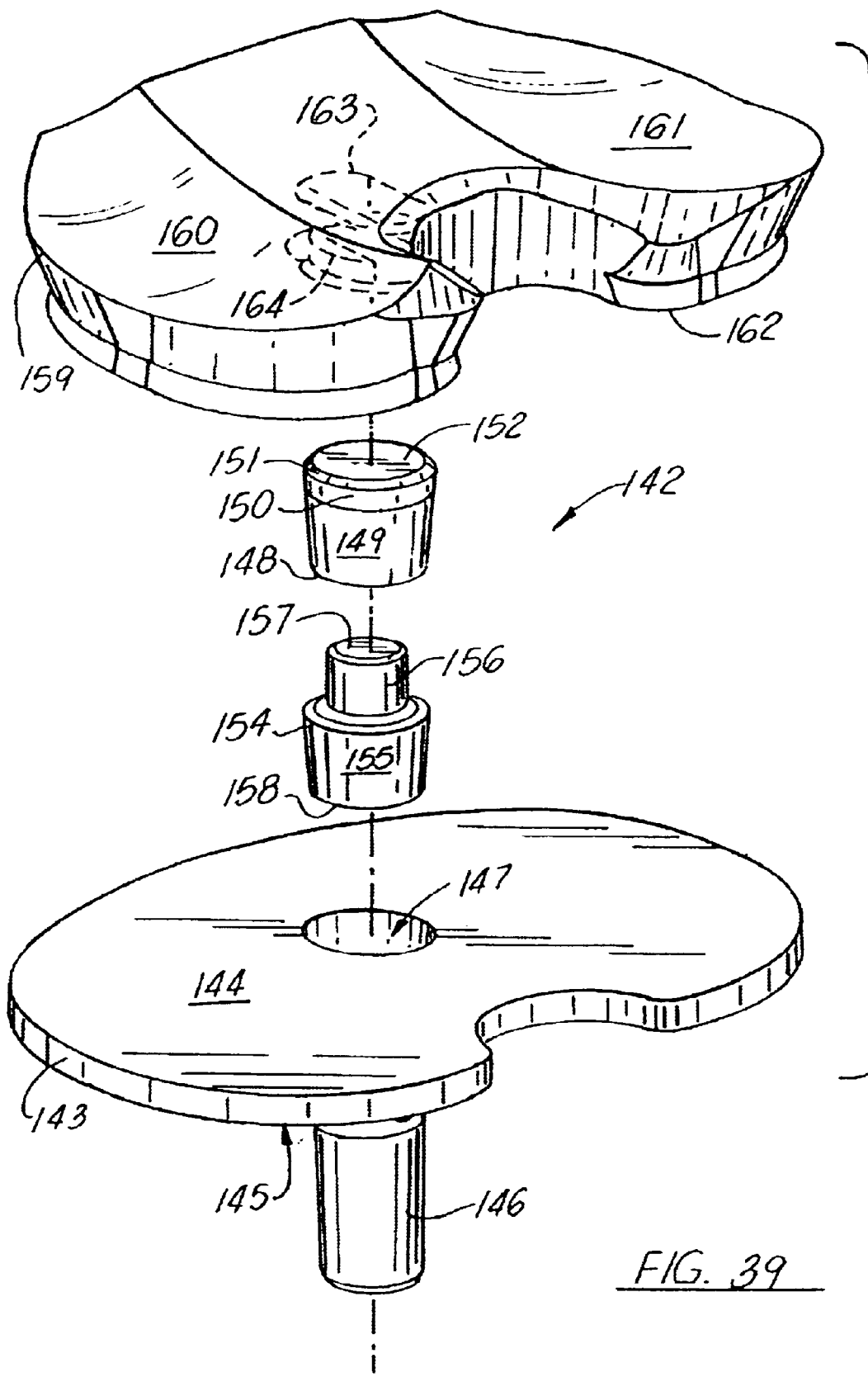
FIG. 39 is a perspective exploded view of a third alternate embodiment of the apparatus of the present invention.
Figure 40:
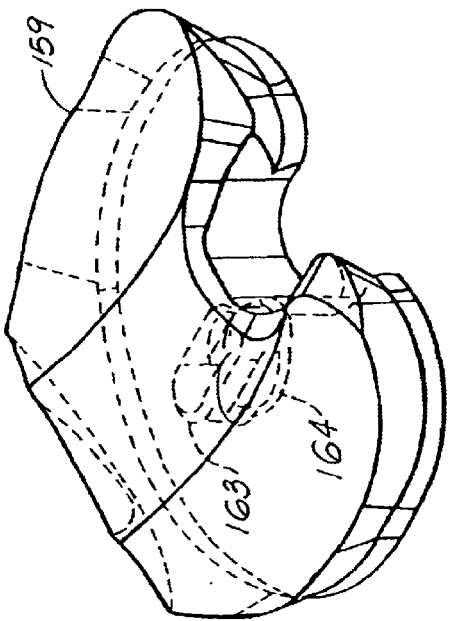
FIG. 40 is a partial top view of the third alternate embodiment of the apparatus of the present invention illustrating the insert portion thereof.
Figure 42:
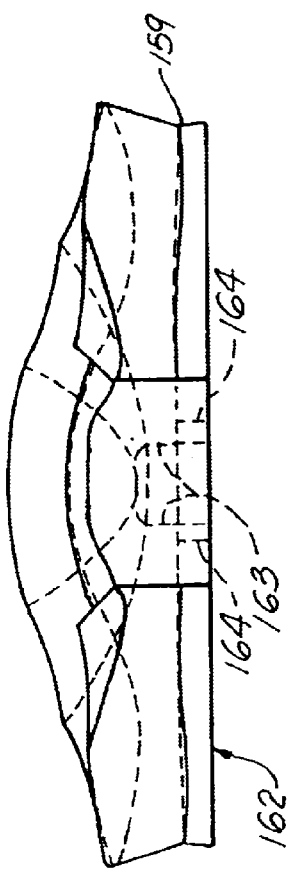
FIG. 42 is a perspective view of the insert portion of the third alternate embodiment of the apparatus of the present invention.
Figure 41:
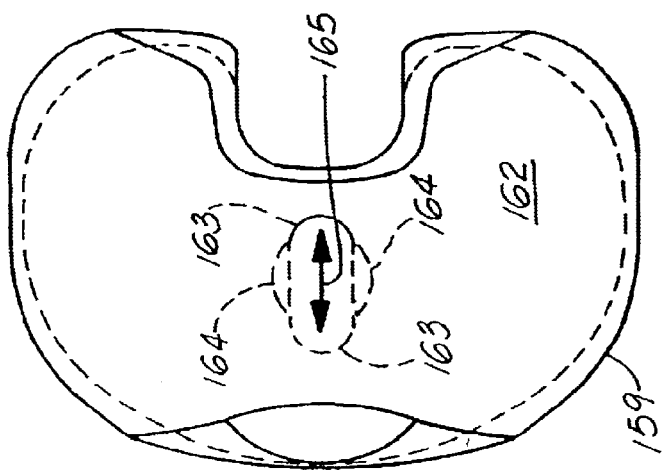
FIG. 41 is a side view of the insert portion of the third alternate embodiment of the apparatus of the present invention.
Figure 43:
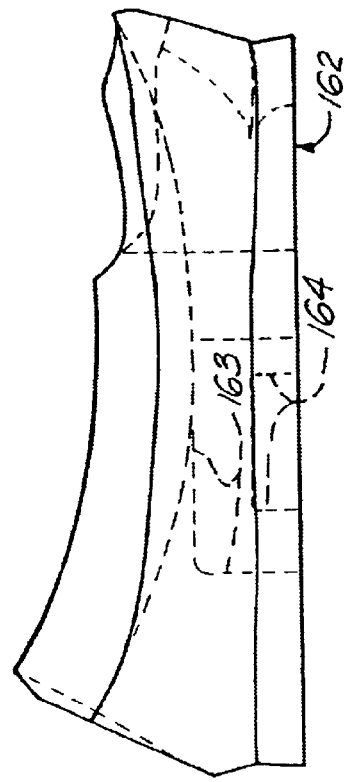
FIG. 43 is a posterior view of the insert portion of the third alternate embodiment of the apparatus of the present invention.
Figure 55:
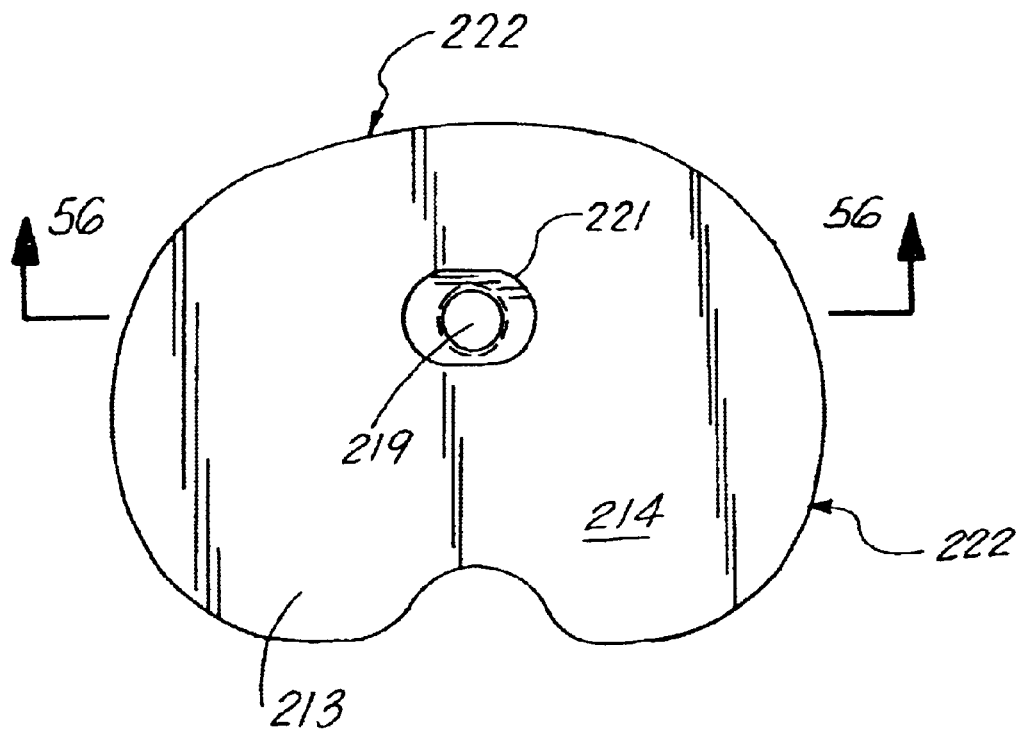
FIG. 55 is a partial top view of the fourth alternative embodiment of the apparatus shown in FIG. 52 illustrating the tray.
Figure 56:
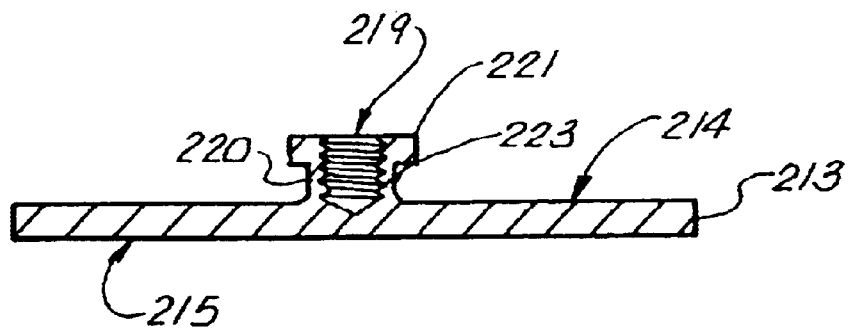
FIG. 56 is a sectional view of the fourth alternative embodiment of the apparatus shown in FIG. 52 taken along lines 56—56 of FIG. 55.

FIGS. 39 and 40–51 show a third alternate embodiment of the apparatus of the present invention designated generally by the numeral 142 in FIG. 39. Mobile bearing knee prosthesis 142 includes a tray 143 that can be attached to a patient's surgically cut proximal tibia using a stem 146 for example that occupies the patient's intramedullary canal. The tray 143 has a proximal surface 144 that receives an insert 159 and a distal surface 145 that registers upon the proximal tibia after the tibia has been surgically prepared to conform to the underside or distal surface 145 of tray 143.

The proximal 144 surface of tray 143 provides a frustoconically-shaped socket 147 that can receive either of two selected plugs 148 or 154 (or any of the plug embodiments shown in FIGS. 18–21). The first plug 148 is designed to provide rotational movement only between insert 159 and tray 143. The plug 148 has a frustoconical surface 149, cylindrical surface 150, beveled annular surface 151, and a pair of opposed generally parallel flat end surfaces 152, 153.

The second plug 154 is designed to provide both anterior to posterior translational movement between the insert 159 and tray 153 as well as rotational movement between the insert 159 and tray 153. The plug 154 has a frustoconical surface 155, a reduced diameter cylindrical surface 156. and flat end surfaces 157, 158.

During use, a surgeon selects either of the plugs 148 or 154. The frustoconical surfaces 149 or 155 form a tight taper lock fit with a correspondingly shaped frustoconical socket 147 that communicates with the proximal 144 surface of tray 143. Once the selected plug 148 or 154. has been inserted into frustoconical socket 147, the insert 159 is placed on the selected plug 148 or 154. The shape of the plug 148 or 154 that is selected determines whether or not the insert 159 can achieve only rotational movement relative to tray 143 or both rotational and anterior to posterior translational movement.

In the case of the plug 148, only rotational movement between the insert 159 and the tray 143 can be attained. The plug 148 is shorter and thus only communicates with the cylindrically-shaped opening 164 on the bottom or distal surface 162 of insert 159. Plug 148 once inserted in socket 147 only enables a rotational movement of the insert 159 on the tray 143. The cylindrical surface 150 of plug 148 corresponds in size and shape to the circular opening 164 to accomplish a relatively close fit between cylindrical surface 150, of plug 148 and cylindrical opening 164 on insert 159.

When both rotational and translational anterior to posterior movement are desired, the surgeon selects the plug 154. The plug 154 is placed in socket 147 so that frustoconical surface. 155 forms a taper lock fit with a correspondingly sized and shaped socket 147 of tray 143. The smaller cylindrically-shaped portion 156 of plug 154 is taller in a proximal to distal direction than the cylindrically-shaped portion 150 of plug 148. The portion 156 fits elongated slot 163 so that the insert 159 can translate in an anterior to posterior direction as the reduced diameter cylindrical portion 156 travels anterior to posterior in the direction of arrow 165 in FIG. 44. However, the insert can also translate along a path 165 that is curved, or along a path 165 that forms an angle with a purely anterior to posterior direction line. The line 165 in FIG. 44 shows such a purely anterior to posterior line as the direction of travel. Because the slot 163 is at least as wide as the diameter of cylindrical portion 156, rotational movement is also available between insert 159 and tray 143. Insert 159 also provides proximal concavities 160, 161 for receiving a femoral component of a knee implant.

FIGS. 52–56 disclose a fourth alternative embodiment of this invention identified as prosthesis 210, comprising a tibial tray 213, a polymeric insert 28, and a locking member 24. In this embodiment, insert 28 and locking member 24 are the same as described above, but flange 221 is generally D-shaped, having a periphery extending laterally in the medial, lateral, and anterior directions from the outer surface of cylindrical section 220, thereby creating recess 223 on the medial lateral and anterior sides of section 220 (see FIGS. 55, 56). As evidenced by the following description. the assembly of prosthesis 210 is essentially identical to that of prosthesis 10 except for the shape of flange 221.

Locking member 24 forms a removable connection with the socket 219. Locking member 24 has an externally cylindrical section 25 that provides threads that correspond to the threads of internally socket 219 so that the locking member 24 can be threaded into the socket 219 as shown in FIG. 54.

In order to assemble insert 28 to tray 213, the distal surface of 29 of insert 28 is placed next to and generally parallel to the proximal surface 214 of tray 213. Post 218 is aligned with vertical channel 33 of insert 28. During assembly of insert 28 to tray 213, the post 218 is oriented to enter the oval opening portion 37 of distal opening 36. Once the distal surface 29 of insert 28 meets proximal surface 214 of tray 213, flange 221 aligns with oval shaped slot 35 of vertical channel 33. After such assembly, insert 28 is held in position by post 218. This retention of insert 228 by post 218 occurs when flange 221 engages flat surface 40 to prevent separation if any rotation at all occurs between insert 28 and tray 213. If no rotation has occurred between insert 28 and tray 213, the oval shaped circular section 37 is sized to allow post 218 to be inserted into or withdrawn from channel 33.

Figure 57:
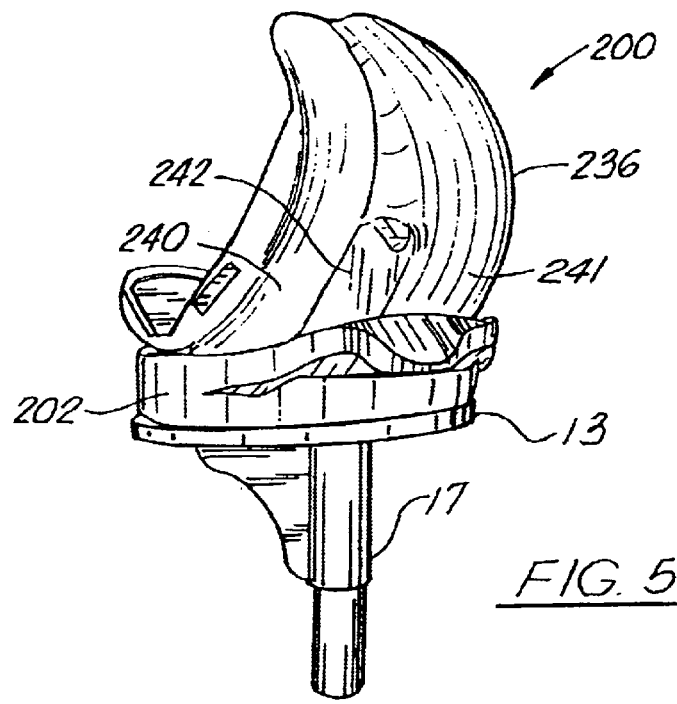
FIG. 57 is a perspective view of a fifth alternate embodiment of the apparatus of the present invention.
Figure 58:
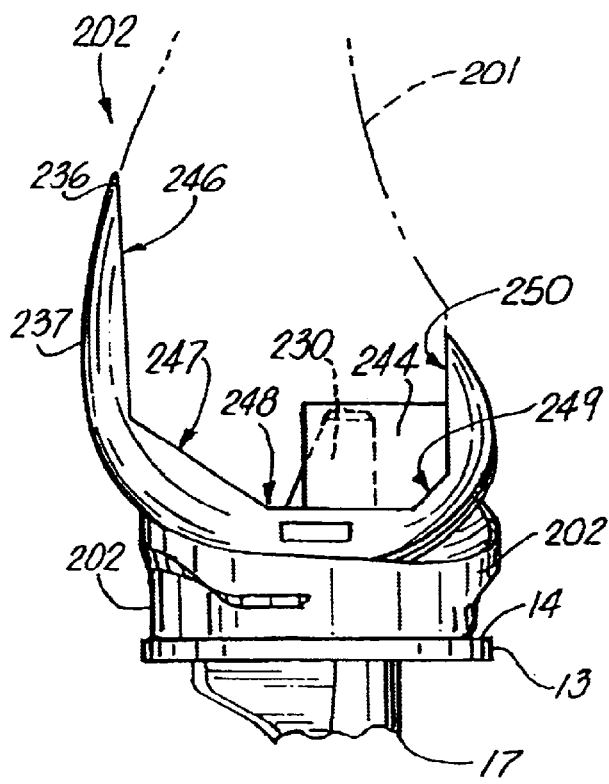
FIG. 58 is a side, elevation view of the fifth alternate embodiment of the apparatus of the present invention.
Figure 59:
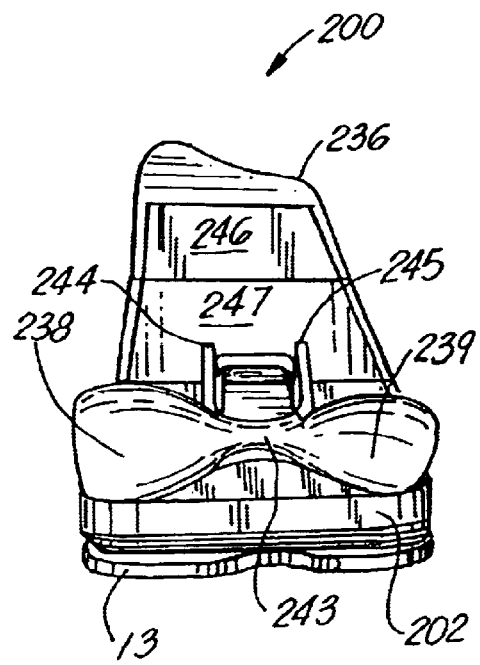
FIG. 59 is a posterior elevation view of a fifth alternate embodiment of the apparatus of the present invention.
Figure 62:
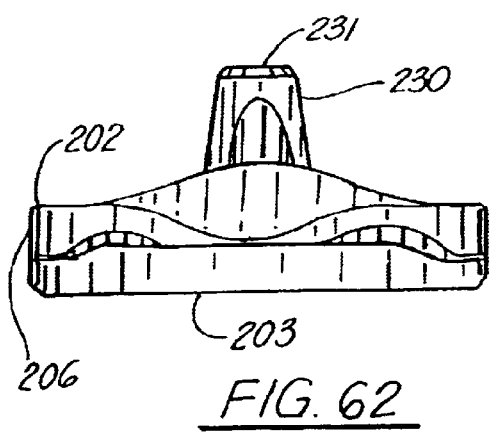
FIG. 62 is a fragmentary anterior elevation view of the fifth alternate embodiment of the apparatus of the present invention showing the polymeric insert.

FIGS. 57–67 show a fifth alternate embodiment of the apparatus of the present invention designated generally by the numeral 200 in FIGS. 57–61. It should be understood that the embodiment of FIGS. 57–67 disclose an alternate construction for a polymeric insert 202 that interconnects with the same tibial tray 13 and stem 17 shown in FIGS. 1, 5–7, 14–16 of the preferred embodiment. In FIGS. 57–59, mobile bearing knee prosthesis 200 is shown as including tray 13, polymeric insert 202, and femoral component 236. In FIG. 58, the femoral component 236 is shown attached to a patient's surgically cut distal femur 201.

Polymeric insert 202 (see FIGS. 62–67) has a flat distal surface 203 and a 25 proximal surface with a pair of concavities 204, 205. Insert 202 also has periphery 206 and vertical channel 207. The vertical channel 207 can be a slotted arrangement such as that shown in the preferred embodiment of FIGS. 1–17 and designated generally by the numeral 33. Thus, the connection between post 18 of tray 13 and insert 202 can be the same connection that is shown and described with respect to the preferred embodiment of FIGS. 1–17 and shown particularly in FIGS. 1–7 and 15–17, or as shown in FIGS. 52–56.

Figure 64:
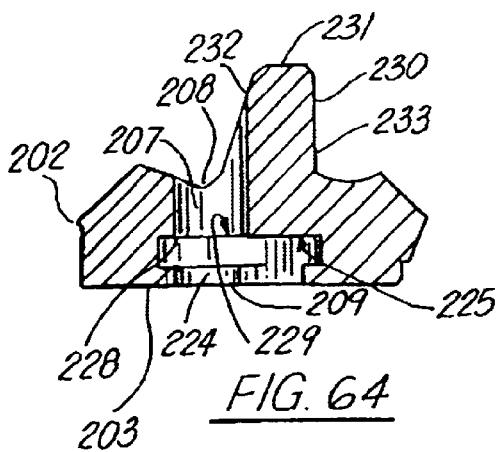
FIG. 64 is a fragmentary side sectional elevation view of the fifth alternate embodiment of the apparatus of the present invention showing the polymeric insert.
Figure 63:
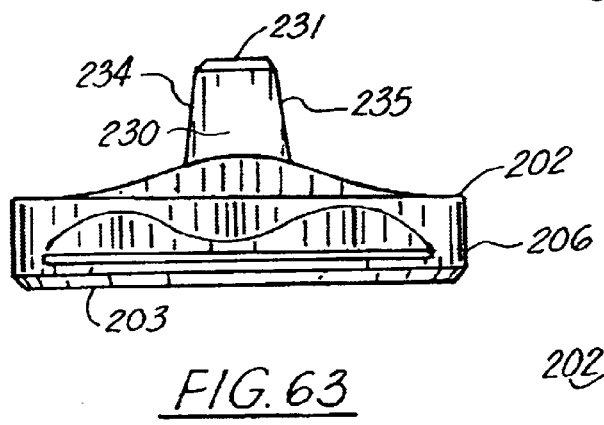
FIG. 63 is a fragmentary posterior elevation view of the fifth alternate embodiment of the apparatus of the present invention showing the polymeric insert.
Figure 66:
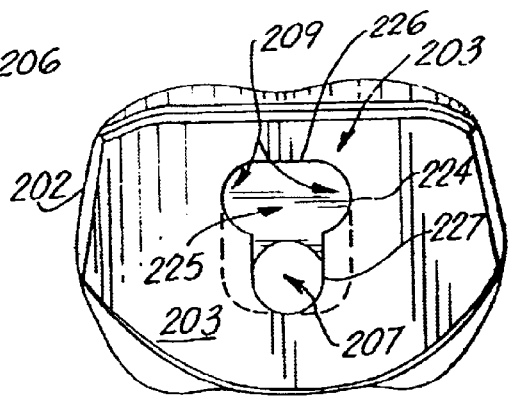
FIG. 66 is a fragmentary bottom view of the fifth alternate embodiment of the apparatus of the present invention showing the polymeric insert.
Figure 65:
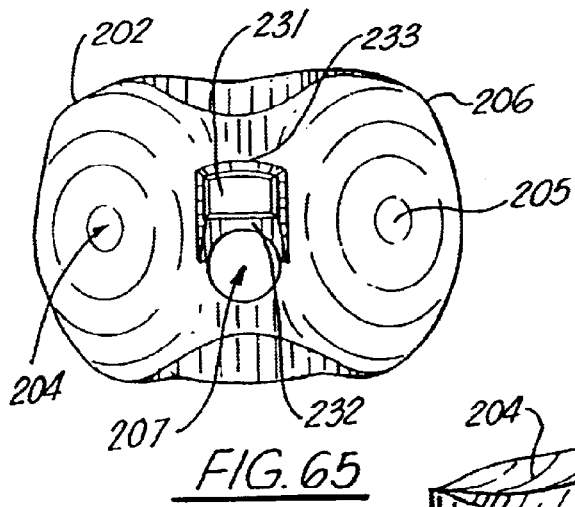
FIG. 65 is a fragmentary plan view of the fifth alternate embodiment of the apparatus of the present invention showing the polymeric insert.
Figure 67:
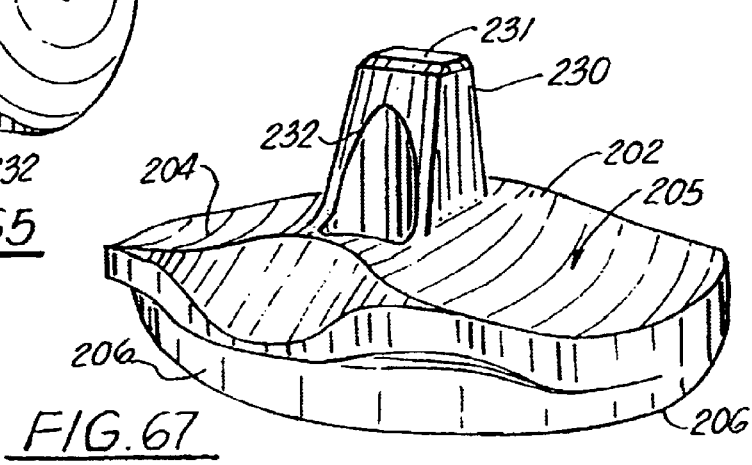
FIG. 67 is a fragmentary perspective view of the fifth alternate embodiment of the apparatus of the present invention showing the polymeric insert.
Figure 69:
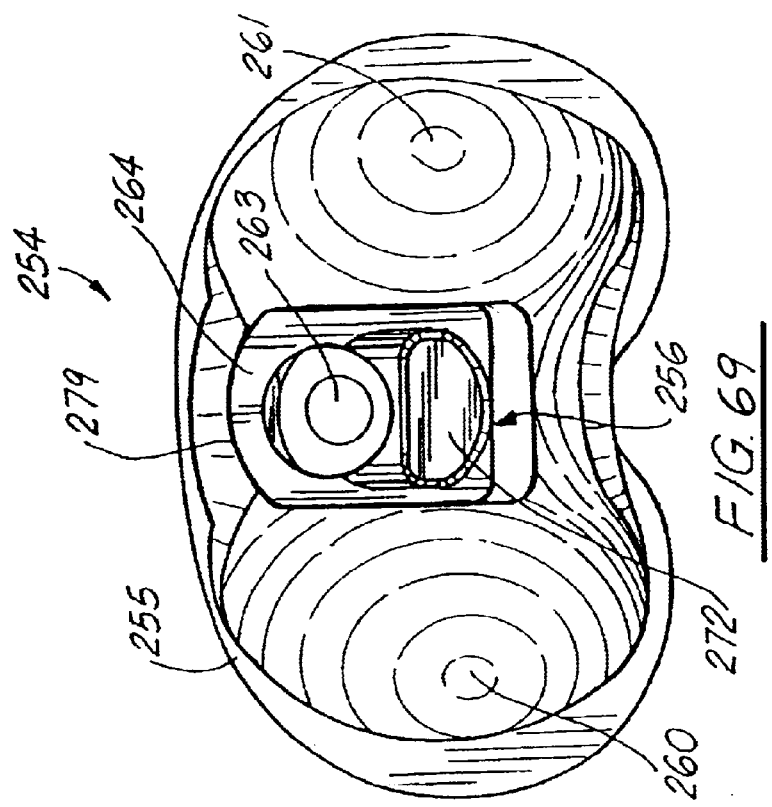
FIG. 69 is a top view of a sixth alternate embodiment of the apparatus of the present invention.

Vertical channel 207 can include a proximal cylindrically shaped section 208, an oval shaped slot 209, and a distal opening 224. The distal opening 224 can include an oval section 226 and a half oval section 227 as shown in FIG. 66. Flat surface 225 extends posteriorly of vertical channel 207 and more particularly posteriorly of the proximal cylindrically shaped section 208, as shown in FIGS. 64 and 65. Flat surfaces 228, 229 register with the flange 21 Of post 18, respectively above and below the flange 21 to thereby prevent separation of polymeric insert 202 from post 18 unless the post 18 is aligned with oval section 226 of distal opening 224. When the flange 21 of post 18 aligns with oval section 226 of distal opening 224, insert 202 can be separated from tray 13.

In the embodiment of FIGS. 57–68, insert 202 provides a central post 230. Post 230 has proximal surface 231 anterior surface 232, posterior surface 233, and sides 234, 235.

Femoral component 236 is shown in FIGS. 57–61. Femoral component 236 has anterior portion 237, a pair of posterior condylar portions 238, 239 and distal condylar portions 240, 241. Femoral component 236 has central opening 242 and a horizontal bar cam 243 that extends between posterior condylar portions 238, 239 as best seen in FIGS. 59. and 68. A pair of vertical walls 244, 245 extend along opposing sides of central opening 242 and connect to both of the posterior condylar portions 238, 239 and to horizontal bar 243. The vertical walls 230, 231 also extend to and connect to surfaces 248, 249, 250. The vertical walls 244, 245 can be generally parallel.

Femoral component 236 provides a plurality of flat surfaces that register against and conform to surgically cut flat surfaces that are provided on the patient's distal femur 201 as shown in FIG. 58. These flat surfaces include flat surface 246 is an anterior surface, surface 247 which is a diagonally extending anterior surface that spans between anterior surface 246 and distal surface 248. Distal surface 248 spans between diagonal surface 247 and posterior diagonal surface 249. Posterior surface 250 is generally parallel to anterior flat surface 246. These five flat surfaces 246–250 of femoral component 236 register against and conform to five surgically cut surfaces on a patient's distal femur 201. Femoral component 236 can be securely fashioned to the patient's distal femur 201 using bone cement for example.

In FIGS. 60 and 61, a range of motion for the patient's knee fitted with mobile bearing knee prosthesis 200 as illustrated with arrows 252, 253. For purposes of reference, the patient's central longitudinal axis 251 of the distal femur 201 is shown rotating posteriorly in the direction of arrow 253. The anterior surface 237 of femoral component 236 is shown rotating in the direction of arrow 252. FIG. 60 shows an extended position of the patient's knee wherein the longitudinal axis 251 of the femur 201 is generally aligned with the central longitudinal axis of the patient's tibia 11. In FIG. 61, the knee is shown in a flexed position. In this position, horizontal bar cam 243 of femoral component 222 registers against the posterior surface 233 of central post 230 of polymeric insert 202. In this position, the central post 230 causes femoral roll back on the tibia articular insert 202. The posterior aspect of the tibia articular surface at 233 provides a lift that is created by generally following the curvature of the femoral component 236 in extension. This will provide a high degree of surface contact, conformity, subsequently providing low contact stress, in extension, where most of gait occurs. The post 230 can have a square or rectangular base that fits snugly within the central opening 242 of the femoral component 236.

By providing the posterior stabilized design with the central post 230, as the knee is flexed, the horizontal bar cam 243 acts as a cam on the femoral component 236 to engage the post 230 at surface 233 on the tibial component 202, causing the femoral posterior condyles 238, 239 to roll back onto the tibial articular concavity surfaces 204, 205. This "roll back" coupled with "climbing" the posterior aspect of the tibial articular surface at 233, causes the femoral component 236 to be located out of the lowest aspect of the tibial articular surfaces 204, 205. With this condition, any type of varust/valgus loading of the joint will cause one of the femoral condyles to apply higher downward loads than the opposing condyle. With a differential in loads, the tibial component 202 will freely spin until the higher loaded condyle displaces to the low point of the tibial articular surface. The central tibial post 216 forces the opposite condyle out of the posterior aspect of the tibial articular surface, thus creating a spin out.

The present invention allows for a free, unlimited rotation of the tibial insert 202 relative to its base plate 13. All of the rotational constraint occurs between the femoral component 236 and the insert 202. The present invention builds conformity of the central post 230 of the insert 202 relative to the box of the femur in rotation, but allowing for varus/valgus tilting. The present invention produces a generally trapezoidal insert post 230.

A sixth alternate embodiment of the apparatus of the present invention is shown in FIGS. 69–81. In the embodiment of FIGS. 66–81, a mobile bearing knee prosthesis 254 features a two-part polymeric insert that includes first member 255 shown in FIGS. 69–75 and a second member 264 shown in FIGS. 69, 76–81. Polymeric insert 255 (see FIGS. 70–75) has a central opening 256 that is bordered by a pair of spaced apart, generally parallel shoulders 257, 258 upon which second member 264 slides fore and aft. The insert 255 has a periphery 259 and a proximal surface with a pair of concavities 260, 261. The insert member 255 includes a flat distal surface 262.

Figure 77:
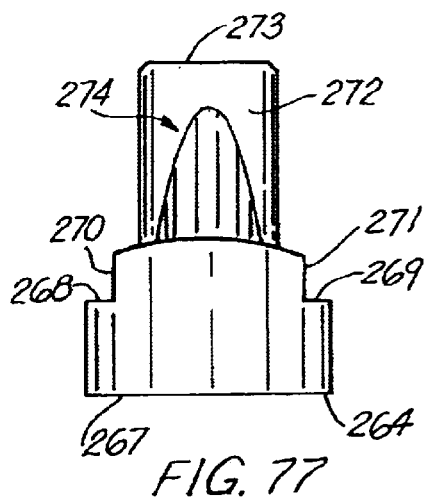
FIG. 77 is a fragmentary rear elevation view of the sixth alternate embodiment of the apparatus of the present invention illustrating one of the polymeric insert portions.
Figure 78:
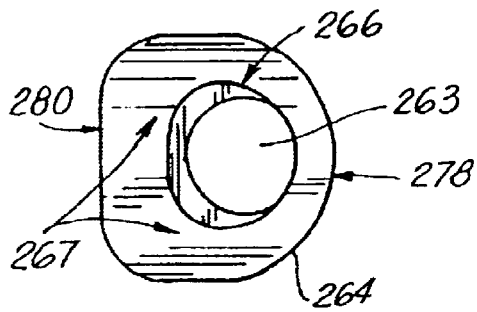
FIG. 78 is a fragmentary bottom view of the sixth alternate embodiment of the apparatus of the present invention illustrating one of the polymeric insert portions.
Figure 79:
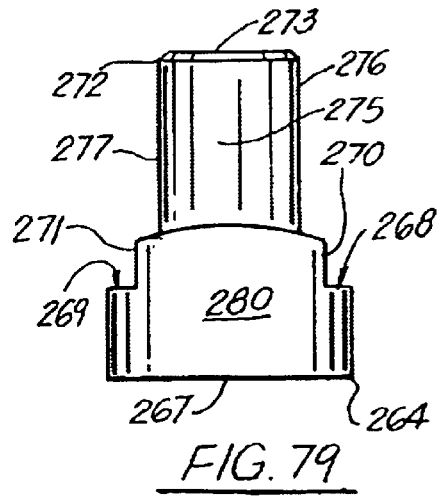
FIG. 79 is a fragmentary, frontal elevation view of the sixth alternate embodiment of the apparatus of the present invention illustrating one of the polymeric insert portions.
Figure 80:
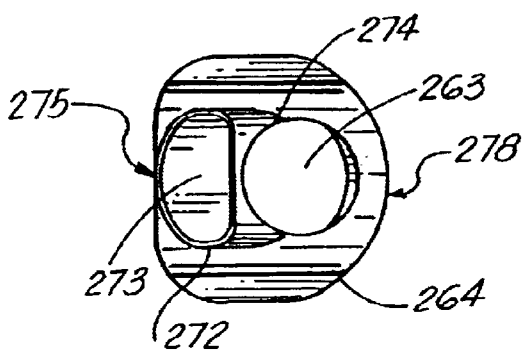
FIG. 80 is a fragmentary, plan view of the sixth alternate embodiment of the apparatus of the present invention illustrating one of the polymeric insert portions.
Figure 81:
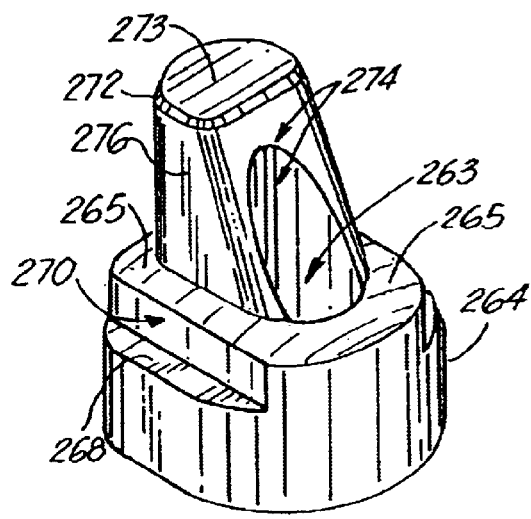
FIG. 81 is a fragmentary, perspective view of the sixth alternate embodiment of the apparatus of the present invention illustrating one of the polymeric insert portions.

The second insert member 264 has a proximal surface 265, a distal surface 267 and a passageway 263 that extends between the surfaces 265,267. A pair of spaced apart, generally parallel shoulders 268, 269 are provided on opposing sides of insert 264 as shown in FIGS. 77, 79 and 81. Flat surfaces 270, 271 are also provided on opposing sides of insert member 264. The surface 270 is generally perpendicular to shoulder 268. The surface 277 is generally perpendicular to the shoulder 267 as shown in FIG. 79.

Insert member 264 provides a post 272. Post 272 has flat, proximal surface 273, anterior surface 274, posterior surface 275, and sides 276, 277. The member 264 provides a curved anterior surface 278 that is correspondingly shaped to and fits against the correspondingly shaped concave surface 279 of member 255 at opening 256.

During use, the shoulders 268, 269 of insert member 264 fit against and slide upon the shoulders 257, 258 of insert member 255. Flat surfaces 270, 271 of insert member 264 engage and slide against flat surfaces 280, 281 of insert 255. The insert. member 264 slides upon the insert member 255 in an anterior to posterior direction because the opening 256 is longer than the insert member 264. The opening 256 is larger in an anterior to posterior direction than the length of the insert member 264 measured from an anterior to posterior direction such as between surfaces 278 and 280.

The present invention includes a posterior stabilizing post 272 secured to the central insert member 264. The posterior stabilized post 272 captures or is captured by bearing insert component 255 to the tibial base plate 13 through an elongated slot or opening 256 in the bearing component 255. The elongated opening or slot 256 in the bearing component member 255 allows it to translate anteriorly and posteriorly with respect to the posterior stabilized post 272 of the insert member 264. The bearing component 255 may also rotate with respect to the tibial base plate 13 in conjunction with the posterior stabilized post 272.

The bearing component 255 has two concave surfaces 260, 261 that are configured to articulate with the convex surfaces (condylar portions) 240, 241 of the femoral component 236 at full extension. The posterior stabilized post 272 articulates with a horizontal bar cam 243 of the femoral component 236 to provide femoral roll back.

The bearing design of the present invention thus consists of a bearing articular insert 255 with a separate posterior stabilized post component 264 that may have one or more degrees of freedom. The bearing articular insert 251 has two concave surfaces 260, 261 that articulate with the convex surfaces (condylar portions) 240, 241 of the femoral component 236 at full extension. The posterior stabilized post 272 articulates with a recess or cam 243 of the femoral component 236 to provide femoral roll back. The, rotational freedom of the posterior stabilized post 272 maintains contact with the femoral bar cam 243 during external or internal rotation of femoral component 236.

The posterior stabilized member 255 has a flat distal surface 262 that articulates with the tibial base plate 13. A tee slot 266 is located on the distal surface 267 and articulates with a tee post 18 on the tibial base plate 13 (see FIGS. 1–17 for such a tee slot and tee post connection). A through hole 263 in the component 264 is located such that a rotation peg (such as peg 24 in FIGS. 1–7) can capture the component 264 to the tibial base plate 13 while the tee slot of the insert component 264 is engaged with a tee post 18 of the tibial base plate. Rotation peg 24 allows only rotational freedom of the insert component 264 with respect to the tibial base plate 13. The elongated slot 256 of the bearing component 255 is larger than the posterior stabilized post carrying component 255 in the anterior-posterior direction such that the bearing component has limited translation with respect to the posterior stabilized post. The bearing component 255 may also rotate with respect to the tibial base plate 13 in conjunction with the posterior stabilized post component 264.

Figure 68:
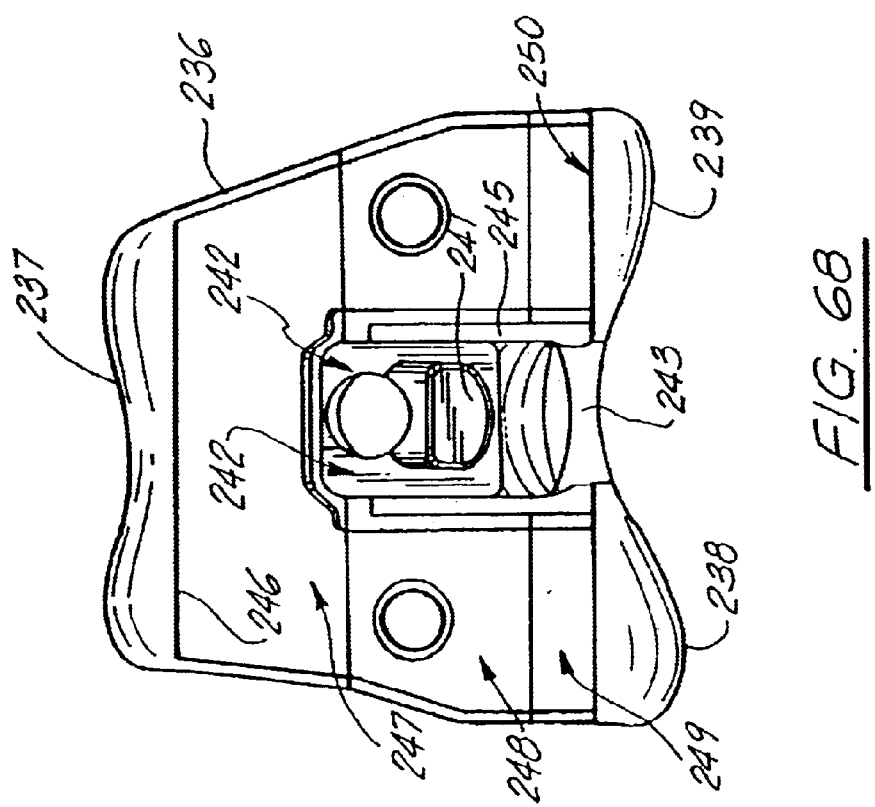
FIG. 68 is a top view of the fifth alternate embodiment of the apparatus of the present invention.
Figure 70:
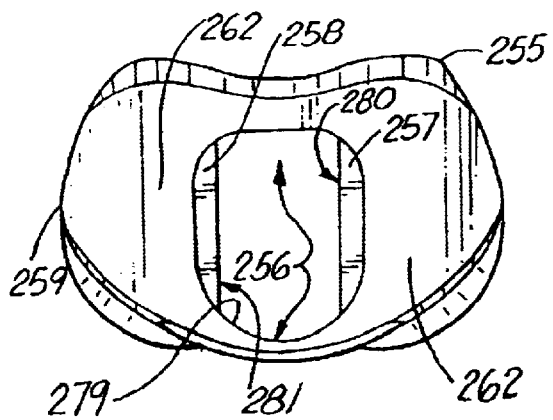
FIG. 70 is a fragmentary bottom view of the sixth alternate embodiment of the apparatus of the present invention showing one of the polymeric insert portions.
Figure 71:
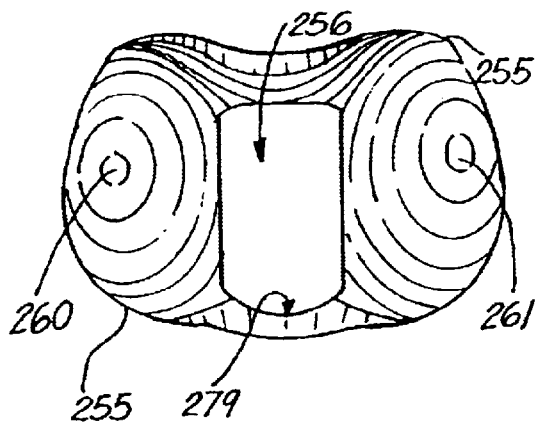
FIG. 71 is a fragmentary top view of the sixth alternate embodiment of the apparatus of the present invention showing one of the polymeric insert portions.
Figure 72:
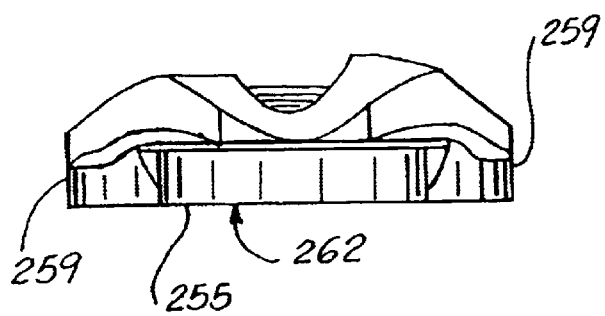
FIG. 72 is a fragmentary, frontal, elevation view of the sixth alternate embodiment of the apparatus of the present invention showing one of the polymeric insert portions.
Figure 73:
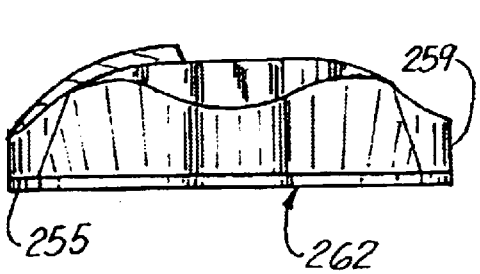
FIG. 73 is a fragmentary rear elevation view of the sixth: alternate embodiment of the apparatus of the present invention showing one of the polymeric insert portions.
Figure 74:
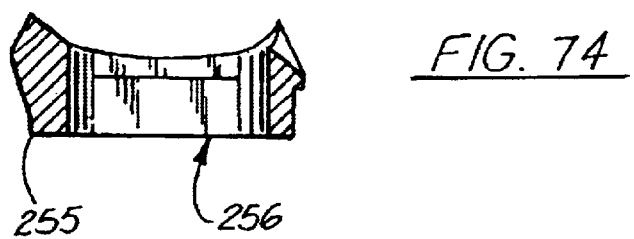
FIG. 74 is a fragmentary side sectional elevation view of the sixth alternate embodiment of the apparatus of the present invention showing one of the polymeric insert portions.
Figure 75:
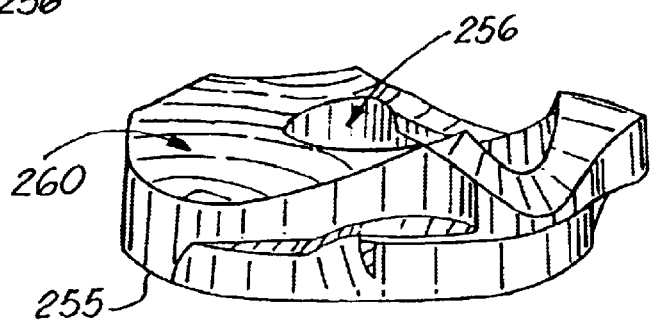
FIG. 75 is a fragmentary perspective view of the sixth alternate embodiment of the apparatus of the present invention showing one of the polymeric insert portions.
Figure 76:
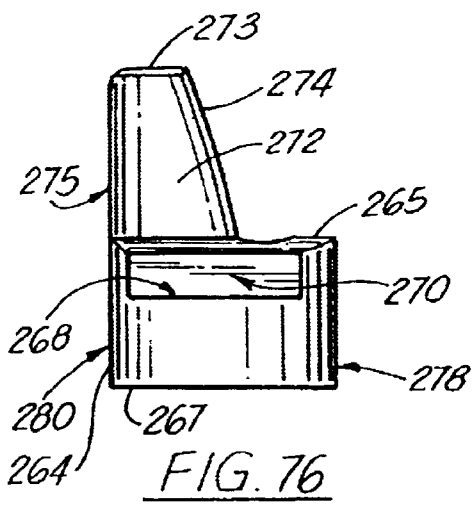
FIG. 76 is a side elevation view of the sixth alternate embodiment of the apparatus of the present invention illustrating one of the polymeric insert portions.

Horizontal bar cam mechanism 243 on the femoral component 236 is preferably a concavely shaped cylinder as shown in FIGS. 59 and 68, that registers against and engages the convex posterior surface 275 of the posterior stabilized post 272. The internal/external rotation of the posterior stabilized post component 264 with the femoral component 236 maintains this contact throughout the range of motion.

As an alternate construction, the second (central) insert member 264 could rotate only with respect to the tibial prosthesis, and the first (peripheral) insert member could both rotate and translate with respect to the tray.

Mobile bearing knee prosthesis 10 is placed upon a patient's surgically cut proximal tibia 11 at a surgically cut proximal surface 12 that is preferably flat. This enables a tray 13 to be mounted to the proximal tibia 11 at surface 12 as shown in FIGS. 6 and 7. Tray 13 has a flat proximal surface 14 and a generally flat distal surface 15 that mates with and faces the surgically prepared surface 12 as shown in FIGS. 6–7. The tray 13 can provide a plurality of spikes 16 and a stem 17 for enhancing implantation to the patient's proximal tibia 11. However, any other known attachment can be used to affix tray 13 to a patient's proximal tibia such as chemical (eg. element) or mechanical fasteners (or fastener).

The proximal surface 14 of tray 13 provides a post 18 having an internally threaded socket 19. Post 18 is comprised of a generally cylindrically-shaped smaller diameter section 20 and an enlarged flange 21 that mounts to the top of cylindrically-shaped 20 as shown in FIGS. 5 and 13–14. Tray 13 has a periphery 22. A recess 23 is provided in between the proximal surface 14 of tray 13 and flange 21.

A locking member 24 forms a removable connection with the socket 19. Locking member 24 has an externally cylindrical section 25 that provides threads that correspond to the threads of internally threaded socket 19 so that the locking member 24 can be threaded into the socket 19 as shown in FIG. 7.

FIGS. 82–94 show a seventh embodiment of the apparatus of the present invention, designated generally by the numeral 283. Mobile bearing knee prosthesis 283 can utilize the same tray 13 of the embodiments of FIGS. 1–81. In FIGS. 82 and 83, a patient's tibia 11 is schematically illustrated as providing a surgically cut proximal surface 12 to which tray 13 is attached. As with the embodiments of FIGS. 1–81, Tray 13 can provide a flat proximal surface 14, a flat distal surface 15, and a stem 17 for attaching the tray 13 to the proximal tibia 11.

A polymeric insert bearing component 284 is shown in FIGS. 82, 83, 84–87 and 93–94. Polymeric insert bearing: component 284 provides a distal surface that can be generally flat. This distal surface 285 can be configured to form an attachment to the proximal surface 14 of tray 13. As with the embodiments shown in FIGS. 1–81, a movable connection can be provided for forming an attachment between tray 13 and polymeric insert bearing component 284. Thus, the tray 13 can be provided with a post 18 as shown in FIGS. 88 and 93 that cooperates with a specialty configured opening 289 at the center of polymeric insert bearing component 284. This connection between post 18 and insert 284 at opening 289 can be the same connection shown and described with respect to any one of the foregoing disclosed embodiments of FIGS. 1–81.

Polymeric insert bearing component 284 can provide a pair of concavities 286, 287 that are receptive of condylar surfaces on femoral component 236. Polymeric insert bearing component, 284 can provide periphery 288, a projecting portion 290, and a posterior projecting portion 292. Projecting portion 290 has a posterior camming surface 291 that communicates with recess 293. A convex surface 295 on posterior projecting portion 292 also communicates with recess 293. At the bottom of recess 293, there is provided a cradle 294 that can be convexly shaped to receive correspondingly shaped concave surface of horizontal bar cam 243 of femoral component 236. As with previously shown and described embodiments of FIGS. 1–81, the femoral component 236 can provide an anterior portion 237, a pair of posterior condylar portions 238, 239 and distal condylar portions 240, 241. As with the embodiments of FIGS. 1–81, femoral component 236 provides a central opening 242 and a horizontal bar cam 243. Vertical walls 244, 245 can also be provided.

The interior of femoral component 236 provides a plurality of surfaces 246–250 that engage surgically cut and correspondingly sized and shaped surfaces on the patient's distal femur 201. The flat surfaces 246, 247, 248, 249 and 250 are shown, for example, in FIGS. 82, 83, 89, 90, 91, and 92.

In the seventh embodiment of the apparatus of the present invention, a mobile bearing knee prosthesis 283 is provided that prevents a "spin out" condition. In mobile bearing tibia designs such as those shown in FIGS. 1–81, the tibia component is able to rotate relative to the femur. In order to provide a posterior stabilized design, the present invention provides an improved arrangement that features a cam projecting portion 290 and hourglass shaped bar 243 arrangement, as shown in FIGS. 82 and 83. The purpose of the cam projecting portion 290 and hourglass shaped bar 243 arrangement of FIGS. 82 and 83 is to force a "roll back" of the femur 201 and femoral component 236 relative to the tibia 11 and the components 13, 284 in flexion (FIG. 83).

Typically, with "roll back" the tibial insert 284 becomes unstable relative to the femoral component 236. Any type of varus/valgus load can force one condyle (240 or 241) of the femoral component 236 to slide down the arc of the articular surface of the tibial insert, thereby forcing the tibial insert to rotate excessively and dislocate from the opposite condyle. When such dislocation occurs, the polymeric tibial insert component 284 is said to have "spun out." With the present invention, such spin out is resisted. The additional projecting portion 292 provides a posterior projecting portion having a convex surface 295. This surface 295 and the posterior cam surface of centrally located projecting portion 290 forms a recess 293 having cradle 294. In a ninety degree (90°) flexion position (see FIG. 83), the horizontal bar 243 which has a generally "hourglass" shape engages projecting portions 292 and 293 within recess 294, as shown, and becomes constrained to restrict further flexion and rotation of femoral component 236 relative to tibial insert 284. Similarly, the polymeric tibial insert 284 is constrained from spinning or rotating, thus avoiding a "spin out" condition.

In FIG. 82, a side view illustrates the position of the components 236, 296, 13, in an extension position. In the extension position, the horizontal bar cam 243 is positioned well above the recess 293 and directly above the convex surface 295 of posterior projecting portion 292. As the patient bends his or her knee to a ninety degree (90°) flexion position shown in FIG. 83, the horizontal bar cam 243 is captured by the recess 293 to prevent relative rotation between the femoral component 236 and the polymeric insert bearing component 284.

In FIG. 82, arrow 296 indicates the contact point between insert. 284 and femoral component 236. This same contact point is designated by arrow 297 in FIG. 83. In FIG. 83, rollback has occurred due to the camming action of projecting portion 290 and its posterior surface 291 with bar 243. In FIG. 84, the contact point is indicated by arrow 298. Arrow 299 schematically illustrates a "rollback" distance from the original contact point 296, 297 and the flexion contact point 298.

PARTS LIST

The following is a list of suitable parts and materials for the various elements of the preferred embodiment of the present invention.

| Part Number | Description |
| --- | --- |
| 10 | mobile bearing knee prosthesis |
| 11 | tibia |
| 12 | surgically cut proximal surface |
| 13 | tray |
| 13A | tray |
| 14 | flat proximal surface |
| 15 | flat distal surface |
| 16 | spike |
| 17 | stem |
| 18 | post |
| 19 | internally threaded socket |
| 20 | cylindrically-shaped section |
| 21 | flange |
| 22 | periphery |
| 23 | recess |
| 24 | fastener |
| 25 | externally threaded section |
| 26 | head |
| 27 | tool receptive socket |
| 28 | insert |
| 29 | flat distal surface |
| 30 | concavity |
| 31 | concavity |
| 32 | periphery |
| 33 | vertical channel |
| 34 | proximal, cylindrically-shaped section |
| 35 | oval shaped slot |
| 36 | distal opening |
| 37 | oval section |
| 38 | half oval section |
| 39 | flat surface |
| 40 | flat surface |
| 41 | arrow/angle |
| 42 | post |
| 43 | cylindrical surface |
| 44 | circular top |
| 45 | rectangular base |
| 46 | inclined side wall |
| 47 | tray socket |
| 48 | inclined surface |
| 49 | post |
| 50 | vertical side wall |
| 51 | inclined surface |
| 52 | flat top |
| 53 | post |
| 54 | vertical side wall |
| 55 | vertical end wall |
| 56 | flat top |
| 57 | rectangular base |
| 58 | inclined surface |
| 59 | post |

-continued

| Part Number | Description |
| --- | --- |
| 60 | flat top |
| 61 | vertical side wall |
| 62 | rectangular base |
| 63 | inclined surface |
| 64 | insert opening |
| 65 | arrow |
| 66 | arrow |
| 110 | mobile bearing knee prosthesis |
| 111 | tibia |
| 112 | surgically cut proximal surface |
| 113 | tray |
| 114 | flat proximal surface |
| 114A | opening |
| 115 | flat distal surface |
| 116 | spike |
| 117 | stem |
| 118 | post |
| 119 | socket |
| 120 | periphery of tray |
| 121 | insert |
| 122 | flat distal surface |
| 123 | proximal surface |
| 124 | concavity |
| 125 | concavity |
| 126 | slot |
| 127 | locking plug member |
| 128 | frustoconical outer surface |
| 129 | socket |
| 130 | threaded bore |
| 131 | locking screw |
| 132 | internally threaded opening |
| 133 | annular shoulder |
| 134 | enlarged annular shoulder |
| 135 | periphery of insert |
| 136 | opening |
| 137 | frustoconical portion |
| 138 | annular reference line |
| 139 | frustoconical surface |
| 140 | enlarged head |
| 141 | arrows |
| 142 | mobile bearing knee prosthesis |
| 143 | tray |
| 144 | proximal surface |
| 145 | distal surface |
| 146 | stem |
| 147 | frustoconical socket |
| 148 | plug |
| 149 | frustoconical surface |
| 150 | cylindrical surface |
| 151 | beveled annular surface |
| 152 | flat end surface |
| 153 | flat end surface |
| 154 | plug |
| 155 | frustoconical surface |
| 156 | reduced diameter cylindncal surface |
| 157 | flat end surface |
| 158 | flat end surface |
| 159 | insert |
| 160 | proximal concavity |
| 161 | proximal concavity |
| 162 | flat distal surface |
| 163 | elongated slot |
| 164 | cylindrical opening |
| 165 | arrow |
| 200 | mobile bearing knee prosthesis |
| 201 | surgically cut femur |
| 202 | polymeric insert |
| 203 | flat distal surface |
| 204 | concavity |
| 205 | concavity |
| 206 | periphery |
| 207 | vertical channel |
| 208 | proximal cylindrically-shaped section |
| 209 | oval shaped slot |
| 210 | mobile bearing knee prosthesis |

-continued

| Part Number | Description |
|---|---|
| 213 | tray |
| 214 | flat proximal surface |
| 215 | flat distal surface |
| 216 | spike |
| 217 | stem |
| 218 | post |
| 219 | internally threaded socket |
| 220 | cylindrically-shaped section |
| 221 | flange |
| 222 | periphery |
| 223 | recess |
| 224 | distal opening |
| 225 | flat surface |
| 226 | oval section |
| 227 | half oval section |
| 228 | flat surface |
| 229 | flat surface |
| 230 | central post |
| 231 | proximal surface |
| 232 | anterior surface |
| 233 | posterior surface |
| 234 | side |
| 235 | side |
| 236 | femoral component |
| 237 | anterior portion |
| 238 | posterior condylar portion |
| 239 | posterior condylar portion |
| 240 | distal condylar portion |
| 241 | distal condylar portion |
| 242 | central opening |
| 243 | horizontal bar cam |
| 244 | vertical wall |
| 245 | vertical wall |
| 246 | flat surface |
| 247 | flat surface |
| 248 | flat surface |
| 249 | flat surface |
| 250 | flat surface |
| 251 | central longitudinal axis |
| 252 | arrow |
| 253 | arrow |
| 254 | mobile bearing knee prosthesis |
| 255 | polymeric insert bearing component |
| 256 | central opening |
| 257 | shoulder |
| 258 | shoulder |
| 259 | periphery |
| 260 | concavity |
| 261 | concavity |
| 262 | distal surface |
| 263 | through hole |
| 264 | central insert component |
| 265 | proximal surface |
| 266 | tee slot |
| 267 | distal surface |
| 268 | shoulder |
| 269 | shoulder |
| 270 | flat surface |
| 271 | flat surface |
| 272 | post |
| 273 | flat proximal surface |
| 274 | anterior surface of post |
| 275 | posterior surface of post |
| 276 | side |
| 277 | side |
| 278 | curved anterior surface |
| 279 | concave surface |
| 280 | posterior surface |
| 281 | flat surface |
| 282 | flat surface |
| 283 | mobile bearing knee prosthesis |
| 284 | polymeric insert hearing component |
| 285 | flat distal surface |
| 286 | concavity |
| 287 | concavity |
| 288 | periphery |
| 289 | opening |

-continued

| Part Number | Description |
|---|---|
| 290 | projecting portion |
| 291 | posterior surface |
| 292 | posterior projecting portion |
| 293 | recess |
| 294 | cradle |
| 295 | convex surface |
| 296 | contact point arrow |
| 297 | contact point arrow |
| 298 | contact point arrow |
| 299 | arrow |

The foregoing embodiments are presented by way of example only; the scope of the present invention is to be limited only by the following claims.

What is claimed is:

1. A knee prosthesis for replacing all or part of a patient's knee joint comprising:

a) a tibial component adapted to be surgically implanted on a patient's transversely cut proximal tibia;

b) a fixator for holding the tibial component on the patient's proximal tibia;

c) a tibial insert having a distal surface that fits against and articulates with the proximal surface of the tibial component and a proximal articulating surface that has a central projecting portion and a posterior projecting portion;

d) a femoral component that articulates with the tibial prosthesis at the proximal articulating, surface of the tibial insert, the tibial insert having condylar surfaces that engage but do not substantially constrain the condylar surfaces of the femoral component;

e) a constraining mechanism that enables a connection to be made between the insert and the tibial component during use; and f) an anti-rotation bar for resisting relative rotation between the femoral component and the tibial insert, including a cam on the femoral component and recess on the tibial component that is posterior to the central projecting portion;

g) wherein the anti-rotation bar engages said projecting portions to prevent rotational dislocation of the tibial insert during flexion.

2. The knee prosthesis of claim 1 wherein a slot extends through the insert, communicating with both the proximal and distal surfaces of the insert, the slot enabling both anterior to posterior translation and rotation of the insert relative to the tibial component.

3. The knee prosthesis of claim 1 wherein the slot has an elongated section that communicates with the distal surface of the insert.

4. The knee prosthesis of claim 1 wherein the slot has a generally cylindrically-shaped section that communicates with the proximal surface of the insert.

5. The knee prosthesis of claim 2 wherein the slot has a larger transverse cross section at the distal surface of the insert and a smaller transverse cross section at the proximal surface of the insert.

6. The knee prosthesis of claim 1 wherein the femoral component includes an intercondylar surface that is positioned to contact the centrally located projecting portion, enabling relative motion between the femoral component and the insert to be constrained.

7. A knee prosthesis apparatus comprising:
   a) a tibial prosthesis configured to be surgically implanted on a patient's transversely cut proximal tibia;
   b) a femoral component;
   c) a fixator for holding the tibial prosthesis on the patient's proximal tibia;
   d) a tibial insert having a proximal surface that is shaped to engage the femoral component, the insert having a distal surface that fits against and articulates with the proximal surface of the tibial prosthesis, the proximal surface of the tibial insert having a pair of spaced apart projecting portions having a slot therebetween, one of the projecting portions being generally centrally positioned on the insert the other projecting portion being positioned on a posterior portion of the insert;
   e) a constraining mechanism that joins the tibial insert to the tibial prosthesis in a selective fashion that enables a number of different possible relative motions between the insert and tibial prosthesis; and
   f) an anti-rotation bar for resisting relative rotation between the femoral component and the tibial insert, including a cam on the femoral component and a recess on the tibial insert that is intermediate said projecting portions; and
   g) wherein the anti-rotation bar engages said projecting portions to prevent rotational dislocation of the tibial insert during flexion.

8. The knee prosthesis of claim 7 wherein the anti-rotation bar rests in said recess when the femoral component is in a full flexion position.

9. The knee prosthesis of claim 7 wherein the cam is generally transversely extending.

10. The knee prosthesis of claim 7 wherein the proximal surface of the insert has one or more concavities for articulating with the femoral component.

11. The knee prosthesis of claim 7 wherein there are two concavities that define articulation surfaces on the proximal surface of the tibial insert.

12. The knee prosthesis of claim 7 wherein the constraining mechanism includes said centrally located projecting portions extending up from the proximal surface of the tibial insert.

13. The knee prosthesis of claim 12 wherein the femoral component includes an intercondylar surface that is positioned to contact the centrally located projecting portion, enabling relative motion between the femoral component and the insert to be constrained.

14. The knee prosthesis of claim 12 wherein the centrally located projecting portion has an inclined posterior surface.

15. The knee prosthesis of claim 7 wherein the femoral component includes an intercondylar surface that is positioned to contact the centrally located projecting portion, enabling relative motion between the femoral component and the insert to be constrained.

16. The knee prosthesis of claim 7 wherein the constraining mechanism includes an opening that extends from the proximal to the distal surface of the insert and a variety of connectable portions which are selectively attachable to or separable from the tray, and wherein the geometry of the various connectable portions relative to the opening enables a user to determine which of the relative motions will take place.

17. A knee prosthesis apparatus comprising:
   a) a tibial component that includes a tibial tray portion adapted to be surgically implanted on a patient's transversely cut proximal tibia;
   b) a femoral component that engages the tibial component, the femoral component having a pair of condyle portions spanned by a posterior, transverse bar;
   c) a post mounted on the proximal surface of the tray, the post having a socket;
   d) the tibial component including a tibial insert having an articulation surface for articulating with the femoral component, the insert having a distal surface that fits against and moves on the proximal surface of the tray;
   e) the insert having a central, generally vertical projecting portion and a posterior generally vertically projecting portion;
   f) a receptacle in between the centrally positioned projecting portion and the posterior projecting portion;
   g) wherein the receptacle has a portion that engages with the bar when the femoral component is rotated upon the tibial component to a ninety degree flexion position.

18. The knee prosthesis of claim 17 wherein the post has a socket that receives the locking plug member.

19. The knee prosthesis of claim 17 further comprising a slot that extends through the insert, communicating with both the proximal and distal surfaces of the insert.

20. The knee prosthesis of claim 17 wherein the slot has a larger transverse cross section at the distal surface of the insert and a smaller transverse cross section at the proximal surface of the insert.

21. The knee prosthesis of claim 17 wherein a channel that extends completely through the insert and the locking member extends through the insert from the proximal surface of the insert to connect with the post.

22. The knee prosthesis of claim 17 wherein the channel closely conforms to the locking member at the proximal surface of the insert.

23. A knee prosthesis apparatus comprising:
   a) a tibial tray portion configured to be surgically implanted on a patient's transversely cut proximal tibia;
   b) a femoral component having a pair of spaced apart posterior condylar portions with an opening therebetween and a bar that spans between the condylar portions at the opening;
   c) a fixator for holding the tray on the patient's proximal tibia;
   d) a tibial insert having a proximal articulation surface that engages the femoral component, the proximal surface including medial and lateral concavities and a first projecting member positioned in between said concavities and occupying said femoral opening during use, the insert having a distal surface that fits against and articulates with the proximal surface of the tray;
   e) a constraining mechanism that joins the insert to the tray during use in a selective fashion that enables a number of different possible relative motions between the insert and tibial tray;
   f) wherein the tibial insert has a second projecting member that is posterior to the first projecting member, and there is a recess in between the first and second projecting members;
   g) the recess capturing the bar when the femoral component patient's knee flexes about ninety degrees.

24. A knee prosthesis apparatus comprising:
   a) a tibial prosthesis configured to be surgically implanted on a patient's transversely cut proximal tibia;
   b) a tibial insert having a distal surface that fits against and articulates with the proximal surface of the tibial component and a proximal articulating surface.

c) a femoral component that articulates with the proximal surface of the insert;

d) a constraining mechanism that joins the insert to the tray during use in a selective fashion that enables a number of different possible relative motions between the insert and tibial tray including anterior to posterior translation and rotation or rotation only;

e) wherein all or part of the constraining mechanism is separable from the tray and selective removal of all or part of the constraining mechanism determines which of the said possible relative motions will take place; and f) a locking mechanism including respective interlocking portions on the femoral component and tibial insert that engage when the knee is in flexion, said interlocking portions including correspondingly shaped concavely and convexly shaped surfaces on the respective interlocking portions.

* * * * *